(12) United States Patent
Yamamoto et al.

(10) Patent No.: US 11,076,828 B2
(45) Date of Patent: Aug. 3, 2021

(54) ULTRASONIC ENDOSCOPE

(71) Applicant: FUJIFILM Corporation, Tokyo (JP)

(72) Inventors: Katsuya Yamamoto, Ashigara-kami-gun (JP); Satoru Okada, Ashigara-kami-gun (JP); Yasuhiko Morimoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 412 days.

(21) Appl. No.: 16/206,743

(22) Filed: Nov. 30, 2018

(65) Prior Publication Data
US 2019/0090847 A1 Mar. 28, 2019

Related U.S. Application Data

(63) Continuation of application No. PCT/JP2017/017841, filed on May 11, 2017.

(30) Foreign Application Priority Data

Jun. 30, 2016 (JP) .............................. JP2016-130195

(51) Int. Cl.
*A61B 8/12* (2006.01)
*A61B 8/00* (2006.01)
(Continued)

(52) U.S. Cl.
CPC .............. *A61B 8/4444* (2013.01); *A61B 8/12* (2013.01); *A61B 8/44* (2013.01); *A61B 8/4483* (2013.01);
(Continued)

(58) Field of Classification Search
CPC ........... A61B 8/12; A61B 8/44; A61B 8/4444; A61B 8/445; A61B 8/4483; A61B 8/4488; A61B 8/546; B06B 1/0622
See application file for complete search history.

(56) References Cited

U.S. PATENT DOCUMENTS

2008/0300492 A1 12/2008 Nagano et al.
2009/0062656 A1 3/2009 Hyuga
(Continued)

FOREIGN PATENT DOCUMENTS

CN 101396289 A 4/2009
EP 0 553 804 A2 8/1993
(Continued)

OTHER PUBLICATIONS

Extended European Search Report, dated Apr. 23, 2019, for European Application No. 17819677.0.
(Continued)

*Primary Examiner* — Mark D Remaly
(74) *Attorney, Agent, or Firm* — Birch, Stewart, Kolasch & Birch, LLP

(57) ABSTRACT

An ultrasonic endoscope has a laminated body that includes an ultrasonic transducer array in which a plurality of ultrasonic transducers are arranged, and a backing material layer that supports the plurality of ultrasonic transducers; a cable portion that includes a plurality of cables each of which is electrically connected to a corresponding one of the plurality of ultrasonic transducers, and a shield member that covers the plurality of cables from outside and that is made of a metal; and a first heat conductive member that is disposed on a side surface of the laminated body. The first heat conductive member is extended to the shield member that is grounded to a housing and is thermally connected to the shield member.

19 Claims, 14 Drawing Sheets

(51) Int. Cl.
  *B06B 1/06* (2006.01)
  *A61B 1/00* (2006.01)
  *A61B 1/018* (2006.01)

(52) U.S. Cl.
  CPC ............ *A61B 8/546* (2013.01); *B06B 1/0622* (2013.01); *A61B 1/0008* (2013.01); *A61B 1/018* (2013.01)

(56) References Cited

U.S. PATENT DOCUMENTS

| | | | |
|---|---|---|---|
| 2009/0088646 A1 | 4/2009 | Nagano et al. | |
| 2009/0234233 A1* | 9/2009 | Nagano | A61B 8/12 600/462 |
| 2014/0046190 A1* | 2/2014 | Ogawa | A61B 8/4444 600/462 |
| 2016/0278737 A1 | 9/2016 | Fujimura | |

FOREIGN PATENT DOCUMENTS

| | | |
|---|---|---|
| EP | 0782125 A2 | 7/1997 |
| EP | 2 644 084 A1 | 10/2013 |
| JP | 2008-295749 A | 12/2008 |
| JP | 2009-240755 A | 10/2009 |
| JP | 2009-297352 A | 12/2009 |
| WO | WO 2016/035362 A1 | 3/2016 |

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2017/017841, dated Jan. 10, 2019, with English translation of the Written Opinion.

International Search Report (form PCT/ISA/210) for International Application No. PCT/JP2017/017841 dated Jul. 11, 2017, with English Translation.

Chinese Office Action and Search Report for corresponding Chinese Application No. 201780040244.4, dated Jan. 26, 2021, with English translation of the Office Action.

Guoqing et al.. "Generic Cabling Technology and Network Engineering," Beijing: China Building Materials Industry Press, May 31, 2015, pp. 14-15.

* cited by examiner

ULTRASONIC ENDOSCOPE

CROSS-REFERENCE TO RELATED APPLICATIONS

This application is a Continuation of PCT International Application No. PCT/JP2017/017841 filed on May 11, 2017, which claims priority under 35 U.S.C. § 119(a) to Japanese Patent Application No. 2016-130195 filed on Jun. 30, 2016. The above application is hereby expressly incorporated by reference, in its entirety, into the present application.

BACKGROUND OF THE INVENTION

1. Field of the Invention

The present invention relates to ultrasonic endoscopes, and, in particular, to an ultrasonic endoscope that has, in a distal end portion thereof, a structure for dissipating heat generated in very small ultrasonic transducers that are used for an ultrasonic endoscope that is inserted into a body cavity.

2. Description of the Related Art

An ultrasonic endoscope is an endoscope that has an ultrasonic observation portion in a distal end portion thereof mainly for the purpose of observing the gallbladder or the pancreas via digestive tract. In the distal end portion of the ultrasonic endoscope, there are heat-generating elements such as ultrasonic transducers and a light source of the endoscope. Because the distal end portion of the ultrasonic endoscope directly contacts the inside of a living body such as a human body, for safety reasons such as prevention of a moderate-temperature burn, it is required that the surface temperature of an insertion portion be lower than or equal to a predetermined temperature.

Moreover, the distal end portion of the ultrasonic endoscope has, in addition to the ultrasonic observation portion, an illumination unit, a suction port, and the like, as with an ordinary endoscope that does not have an ultrasonic observation portion. Therefore, the outside diameter of the distal end portion of the ultrasonic endoscope is large, which causes reduction in operability of the ultrasonic endoscope and increase of a burden on a patient into whom the distal end portion of the ultrasonic endoscope is inserted.

For this reason, an ultrasonic endoscope that has means for lowering the surface temperature of the distal end portion while maintaining the small size of the distal end portion is required. Therefore, in recent years, various proposals for dissipating heat generated in the ultrasonic transducers have been made (see JP2009-240755A and JP2009-297352A).

JP2009-240755A discloses an ultrasonic endoscope that has an exterior member that covers each portion of the ultrasonic endoscope, a backing material layer that is disposed on back surfaces of a plurality of ultrasonic transducers, a signal-wire housing portion that includes a group of shield wires that are electrically connected to the plurality of ultrasonic transducers and a highly heat conductive filler that closely adheres to the backing material layer, and a highly heat conductive layer that is disposed in contact with the signal-wire housing portion and the exterior member. With this structure, heat generated in the ultrasonic transducers is diffused to the filler via a back surface of the backing material layer or the group of shield wires, and the heat of the filler is further diffused to the surface of the exterior member via the highly heat conductive layer.

An ultrasonic probe disclosed in JP2009-297352A has a piezoelectric portion that emits ultrasound, a ground wire that is connected to the piezoelectric portion and a heat dissipation plate, a heat conductive portion that thermally connects a probe case and the heat dissipation plate, a cable ground wire that is connected to the heat dissipation plate, and a cooling portion that is connected to the cable ground wire and that cools the cable ground wire. It is disclosed that the cable ground wire is grounded in the cooling portion. With this structure, heat generated in the ultrasonic transducers is conducted, via the ground wire and the heat dissipation plate, to the probe case and the cable ground wire that is cooled by the cooling portion; and thereby the heat is dissipated.

SUMMARY OF THE INVENTION

The technology disclosed in JP2009-240755A takes into consideration only a heat dissipation path that dissipates heat generated in the ultrasonic transducers and the backing material layer to the exterior member via the heat conductive member. Therefore, the technology has a problem in that further improvement of heat dissipation efficiency cannot be expected. Moreover, because the technology disclosed in JP2009-240755A uses only the heat dissipation path to the exterior member, heat is dissipated to the inside of a body cavity near the distal end portion of the ultrasonic endoscope. Therefore, the technology has a problem in that, in a case where the drive voltage of the ultrasonic transducers is increased, the temperature of a region around the distal end portion of the ultrasonic endoscope is increased.

In the technology disclosed in JP2009-297352A, because the ultrasonic probe is mainly used for an ultrasonic diagnostic apparatus used for observing the body surface, the diameter of the ground wire and the size of the heat dissipation plate are large. Therefore, the technology has a problem in that, although heat generated in the ultrasonic probe can be dissipated via the ground wire connected to the piezoelectric portion, it is difficult to achieve sufficiently high heat dissipation performance in an ultrasonic endoscope that has only a small space in the distal end portion.

Examples of means that need to be used to improve the diagnosis accuracy of the ultrasonic observation portion in the ultrasonic endoscope or the ultrasonic probe disclosed in JP52009-240755A or JP2009-297352A include increasing ultrasound transmitting power by laminating ultrasonic transducers, increasing sensitivity in receiving an ultrasonic echo by increasing the number of ultrasonic transducers, and increasing the drive voltage of the plurality of ultrasonic transducers. When such means is used, the amount of heat dissipated from the plurality of ultrasonic transducers increases, and therefore the heat causes an increase in the temperature of the insertion portion of the ultrasonic endoscope that contacts the inner wall of a body cavity of a patient, in particular, the temperature of the surface of the distal end portion of the ultrasonic endoscope in which the plurality of ultrasonic transducers are disposed.

There is a problem in that, although improvement of accuracy in ultrasonic diagnosis is required in addition to improvement of operability and relieving of a burden on a patient, it is very difficult to efficiently dissipate heat generated in the distal end portion of the ultrasonic endoscope while maintaining the small diameter of the insertion portion of the ultrasonic endoscope and maintaining the small size of the distal end portion.

An object of the present invention is to solve the problems of the existing technology described above and to provide an ultrasonic endoscope that has a heat dissipation structure that can efficiently dissipate heat generated in ultrasonic transducers while maintaining the small diameter of an insertion portion and maintaining the small size of a distal end portion, and, as a result, that can improve the diagnosis accuracy in ultrasonic observation.

In order to achieve the object, an ultrasonic endoscope according to the present invention includes a laminated body that includes an ultrasonic transducer array in which a plurality of ultrasonic transducers are arranged, and a backing material layer that supports the plurality of ultrasonic transducers; a cable portion that includes a plurality of cables each of which is electrically connected to a corresponding one of the plurality of ultrasonic transducers, and a shield member that covers the plurality of cables from outside and that is made of a metal; and a first heat conductive member that is disposed on a side surface of the laminated body. The first heat conductive member is extended to the shield member that is grounded to a housing and is thermally connected to the shield member.

Preferably, the ultrasonic endoscope according to the present invention further includes a first insulation tube that covers the cable portion, an electroconductive connection pipe that covers a part of the first insulation tube on a proximal end side of the ultrasonic endoscope, a second insulation tube that is connected to one end of the connection pipe on the proximal end side and that covers a part of the connection pipe and a part of the first insulation tube on the proximal end side of the ultrasonic endoscope, and a second heat conductive member that is disposed in contact with both of the first insulation tube and the connection pipe.

Preferably, the second heat conductive member fills at least a part of a space between the first insulation tube and the connection pipe.

Preferably, the second heat conductive member is a cylindrical member that is disposed between the first insulation tube and the connection pipe.

Preferably, the second heat conductive member has a thick portion at an end portion thereof on a distal end side of the ultrasonic endoscope, the thick portion being thicker than a portion thereof that is disposed between the first insulation tube and the connection pipe; and the thick portion contacts an end surface of the connection pipe on the first heat conductive member side.

Preferably, the second heat conductive member includes a cylindrical portion and the thick portion, the cylindrical portion being disposed between the first insulation tube and the connection pipe, and the thick portion is an outward flange that has a cylindrical shape having an outside diameter larger than or equal to an inside diameter of the connection pipe.

Preferably, the cable portion has a jacket of one layer outside of the shield member, and the jacket of the cable portion is removed at least at a portion that is covered by the second heat conductive member together with the first insulation tube.

Preferably, the jacket of the cable portion is removed on the distal end side of the connection pipe and the shield member is exposed; at a portion where the jacket is removed and the shield member is exposed to the first insulation tube, a part of the first insulation tube is removed, and the shield member is exposed to the outside; and the second heat conductive member contacts the portion where the shield member is exposed to the outside, covers the removed part of the first insulation tube, and contacts the distal end side of the connection pipe.

Preferably, the ultrasonic endoscope according to the present invention further includes an insulation layer that is disposed outside of the connection pipe.

Preferably, the ultrasonic endoscope according to the present invention further includes a third heat conductive member that fills a space between the first insulation tube, and a portion of the connection pipe on the proximal end side and the second insulation tube.

With the present invention, because the distal end portion of the ultrasonic endoscope has a heat dissipation structure for dissipating heat toward the proximal end side of the ultrasonic endoscope, it is possible to efficiently dissipate heat that is generated due to driving of the ultrasonic transducers, and it is possible to increase the output power of the ultrasonic transducers without increasing a burden on a patient.

DESCRIPTION OF THE PREFERRED EMBODIMENTS

First Embodiment

Figure 1:
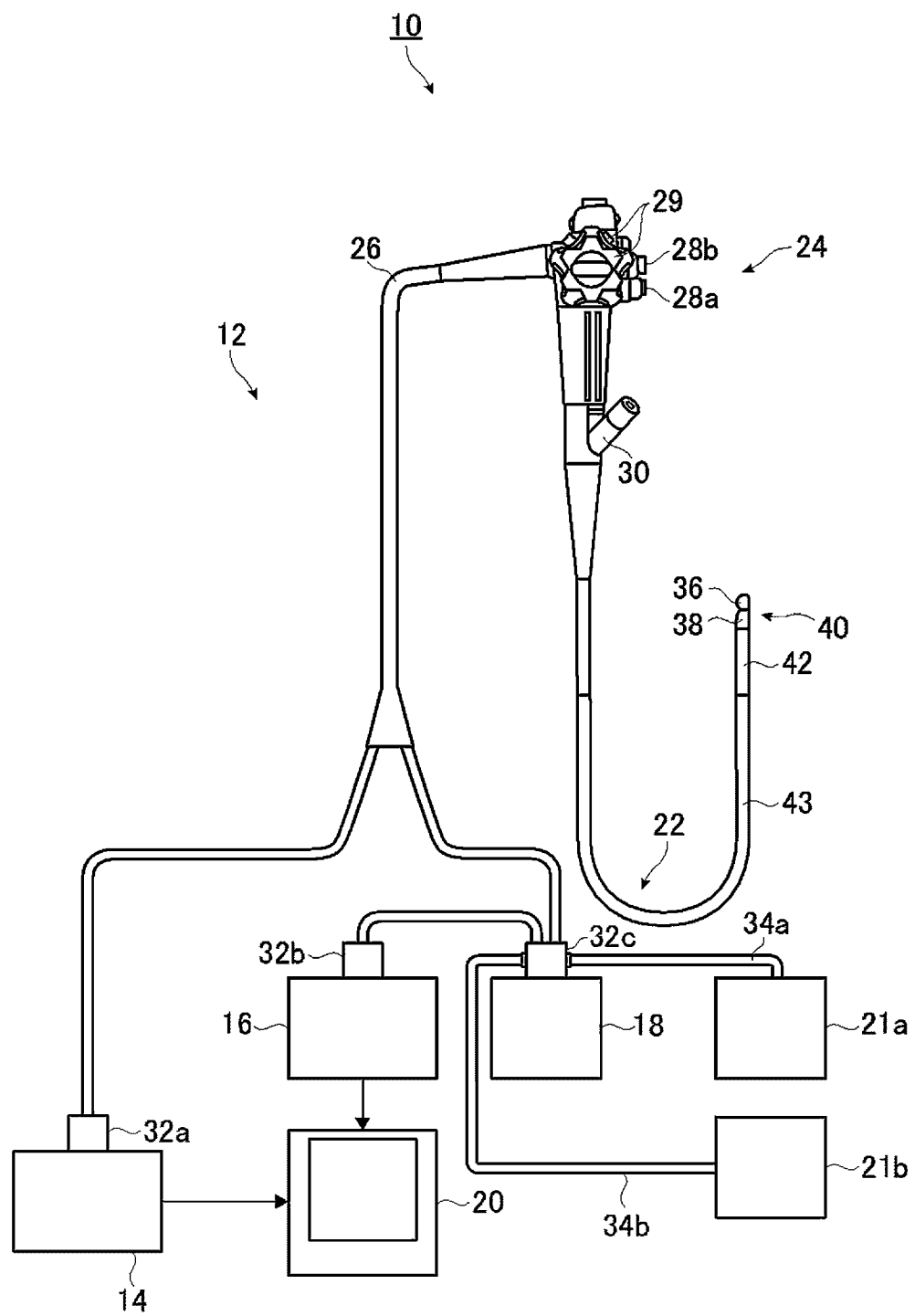
FIG. 1 is a schematic view of an example of the structure of an ultrasonic inspection system that uses an ultrasonic endoscope to which an ultrasonic transducer unit according to the present invention is applied.

Hereinafter, an ultrasonic endoscope according to the present invention will be described in detail based on preferred embodiments illustrated in the drawings.

FIG. 1 is a schematic view of an example of the structure of an ultrasonic inspection system that uses the ultrasonic endoscope according to the present invention.

An ultrasonic inspection system 10 shown in FIG. 1 is a system that enables observation of the gallbladder or the pancreas, which is difficult to observe by using ultrasonic inspection from the body surface of a subject such as a patient, via digestive tract such as the esophagus, the stomach, the duodenum, the small intestine, the large intestine, and the like, each of which is a body cavity of the subject. The ultrasonic inspection system 10 inserts an ultrasonic endoscope according to the present invention, which has an ultrasonic observation portion that captures an ultrasound tomographic image (hereinafter, referred to an ultrasound image) and an endoscopic observation portion that captures an endoscopic optical image (hereinafter, referred to as an endoscopic image), into a body cavity of a subject and captures the ultrasound image of an observation target site of the subject while observing the endoscopic image of the subject.

As illustrated in FIG. 1, the ultrasonic inspection system 10 includes an ultrasonic endoscope 12 having a heat dissipation structure that is a feature of the present invention, an ultrasonic processor device 14 that generates an ultrasound image, an endoscope processor device 16 that generates an endoscopic image, a light source device 18 that supplies illumination light for illuminating the inside of a body cavity to the ultrasonic endoscope 12, and a monitor 20 that displays the ultrasound image and/or the endoscopic image.

The ultrasonic inspection system 10 further includes a water supply tank 21a that stores cleaning water or the like and a suction pump 21b that suctions a suction object (including the supplied cleaning water and the like) in a body cavity. Although not illustrated, the ultrasonic inspection system 10 may include a supply pump or the like that supplies cleaning water in the water supply tank 21a or a gas, such as outside air, to a pipe line (not shown) in the ultrasonic endoscope 12.

First, the ultrasonic endoscope 12 shown in FIG. 1 has, at the distal end thereof, an ultrasonic observation portion 36, having a heat dissipation structure that is a feature of the present invention, and an endoscopic observation portion 38. The ultrasonic endoscope 12 captures an ultrasound image (echo signal) and an endoscopic image (image signal) of the inside of the body cavity.

The ultrasonic endoscope 12 is composed of an insertion portion 22 that includes the ultrasonic observation portion 36 and the endoscopic observation portion 38 at an end thereof and that is inserted into a body cavity of a subject; an operating unit 24 that is connected to a proximal end portion of the insertion portion 22 and with which an operator, such as a doctor or an engineer, performs an operation; and a universal cord 26 one end of which is connected to the operating unit 24.

The operating unit 24 has an air/water supply button 28a, for opening or closing an air/water supply pipe line (not shown) from the water supply tank 21a, and a suction button 28b, for opening or closing a suction pipe line (not shown) from the suction pump 21b, which are arranged side by side. Moreover, the operating unit 24 has a pair of angle knobs 29 and a treatment tool insertion port 30 (forceps port).

Here, the water supply tank 21a stores cleaning water or the like that is supplied to the air/water supply pipe line in the ultrasonic endoscope 12 for cleaning the endoscopic observation portion 38 of the ultrasonic endoscope 12 and the like. The air/water supply button 28a is used to eject a gas such as air and water such as cleaning water, which are supplied from the water supply tank 21a through the air/water supply pipe line, from the endoscopic observation portion 38 on the distal end side of the insertion portion 22.

The suction pump 21b suctions a suction pipe line (not shown) to suction a suction object (including supplied cleaning water and the like) in a body cavity from the distal end side of the ultrasonic endoscope 12. The suction button 28b is used to suction a suction object in a body cavity from the distal end side of the insertion portion 22 by using a suction force of the suction pump 21b.

The treatment tool insertion port 30 is used to insert a treatment tool, such as forceps, a puncture needle, a high-frequency knife, or the like.

At the other end portions of the universal cord 26, an ultrasound connector 32a connected to the ultrasonic processor device 14, an endoscope connector 32b connected to the endoscope processor device 16, and a light source connector 32c connected to the light source device 18 are provided. The ultrasonic endoscope 12 is removably connected to the ultrasonic processor device 14, the endoscope processor device 16, and the light source device 18 via the connectors 32a, 32b, and 32c, respectively. An air/water supply tube 34a, for connecting to the water supply tank 21a, a suction tube 34b, for connecting the suction pump 21b, and the like are connected to the light source connector 32c.

The insertion portion 22 is composed of, in order from the distal end side, a distal end portion 40 (distal end rigid portion) that is formed of a rigid member and that has the ultrasonic observation portion 36 and the endoscopic observation portion 38; a bending portion 42 that is connected to the proximal end side of the distal end portion 40, that is formed by coupling a plurality of bending pieces, and that can be bent freely; and a soft portion 43 that couples the proximal end side of the bending portion 42 and the distal end side of the operating unit 24 to each other, that has a thin and elongated shape, and that has flexibility.

The bending portion 42 is remote-controlled so as to be bent by rotating the pair of angle knobs 29 of the operating unit 24. Therefore, the distal end portion 40 can be directed in a desired direction.

A balloon, which covers the ultrasonic observation portion 36 and into which an ultrasound transmission medium (such as water, oil, or the like) is injected, may be removably attached to the distal end portion 40. Because ultrasound and an echo signal are considerably attenuated in air, by inflating the balloon by injecting the ultrasound transmission medium into the balloon and causing the balloon to contact an observation target site, it is possible to remove air from a space between an ultrasonic transducer array 50 (see FIGS. 2 to 4) of the ultrasonic observation portion 36 and the observation target site and to prevent attenuation of the ultrasound and the echo signal.

The ultrasonic processor device 14 generates and supplies an ultrasound signal (data), for generating ultrasound, to the ultrasonic transducer array 50 (see FIGS. 2 to 4) of an ultrasonic transducer unit 46 of the ultrasonic observation portion 36 of the distal end portion 40 of the insertion portion 22 of the ultrasonic endoscope 12. Moreover, the ultrasonic processor device 14 receives and obtains an echo signal (data), which is reflected from an observation target site to which ultrasound is emitted, with the ultrasonic transducer array 50; and generates an ultrasound image, which is to be displayed on the monitor 20, by performing various types of signal (data) processing on the obtained echo signal.

The endoscope processor device 16 receives and obtains a captured image signal (data) that is obtained from an observation target site, which is illuminated with illumination light from the light source device 18, in the endoscopic observation portion 38 of the distal end portion 40 of the insertion portion 22 of the ultrasonic endoscope 12. The endoscope processor device 16 generates an endoscopic image, which is to be displayed on the monitor 20, by performing various types of signal (data) processing on the obtained image signal.

The processor devices 14 and 16 may be composed of a processor such as a personal computer (PC) or the like.

In order to obtain an image signal by capturing an image of an observation target site in a body cavity by using the endoscopic observation portion 38 of the ultrasonic endoscope 12, the light source device 18 generates illumination light, such as white light or a specific wavelength light, composed of three primitive color light that is, for example, red light (R), green light (G), and blue light (B), and supplies the illumination light to the ultrasonic endoscope 12. The illumination light propagates via a light guide (not shown) or the like in the ultrasonic endoscope 12, is emitted from the endoscopic observation portion 38 of the distal end portion 40 of the insertion portion 22 of the ultrasonic endoscope 12, and illuminates the observation target site in the body cavity.

The monitor 20 receives image signals generated by the ultrasonic processor device 14 and the endoscope processor device 16 and displays an ultrasound image and an endoscopic image. An image to be displayed on the monitor 20 can be switched between the ultrasound image and the endoscopic image, and both of these images can be simultaneously displayed on the monitor 20. A monitor for displaying the ultrasound image and a monitor for displaying an endoscopic image may be independently provided, or the ultrasound image and the endoscopic image may be displayed in any other appropriate form.

Next, referring to FIGS. 2 to 4, the structure of the distal end portion of the insertion portion of the ultrasonic endoscope will be described in detail.

Figure 2:
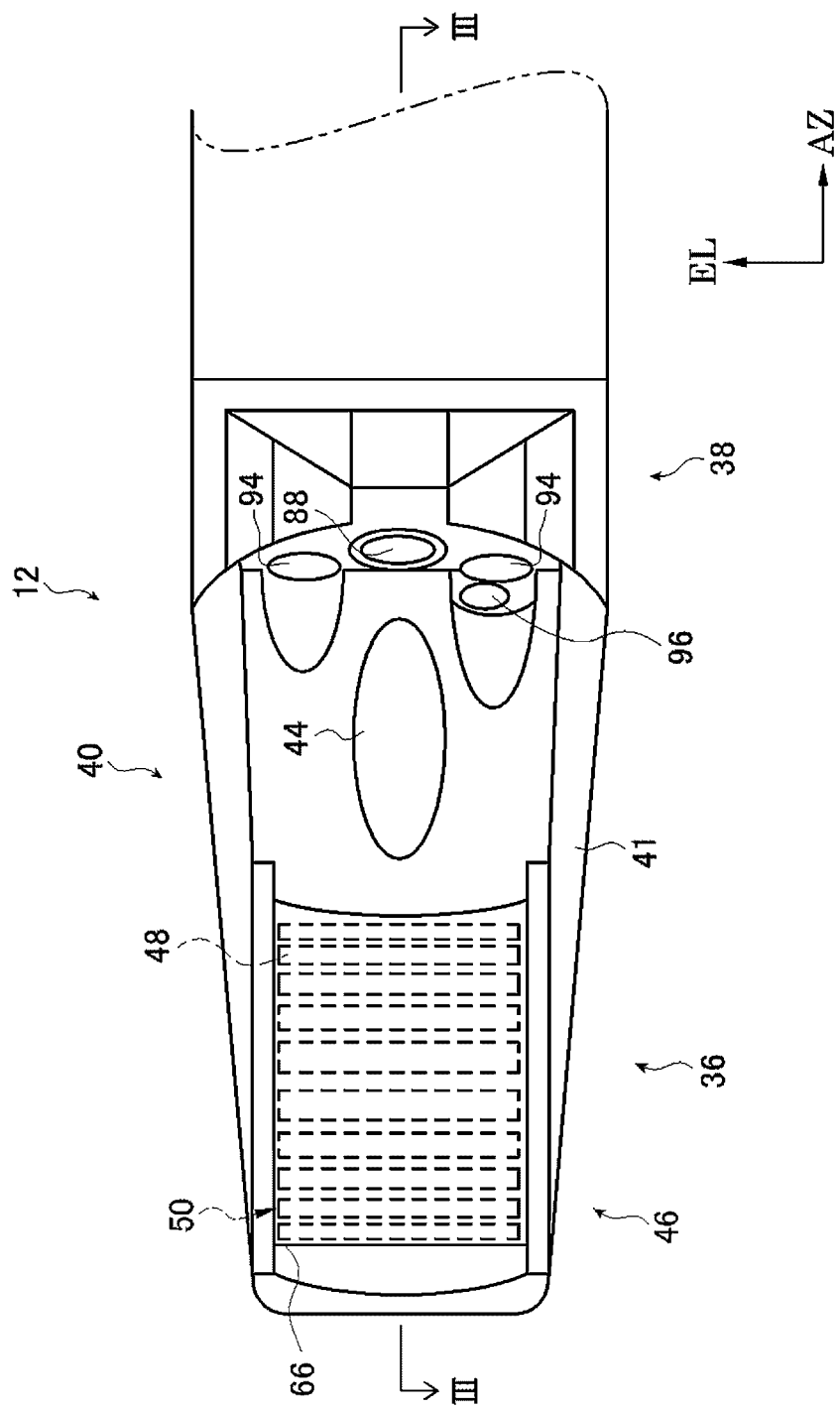
FIG. 2 is a partial enlarged plan view of a distal end portion of an insertion portion of the ultrasonic endoscope shown in FIG. 1.

FIG. 2 is a partial enlarged plan view of the distal end portion of the insertion portion of the ultrasonic endoscope shown in FIG. 1 and the vicinity of the distal end portion. FIG. 3 is a partial longitudinal sectional view taken along line III-III in FIG. 2, illustrating the distal end portion of the insertion portion of the ultrasonic endoscope shown in FIG. 2 that is cut along the centerline in the longitudinal direction thereof. FIG. 4 is a schematic partial longitudinal sectional view of a heat dissipation structure of the distal end portion of the insertion portion of the ultrasonic endoscope shown in FIGS. 1 to 3.

Figure 3:
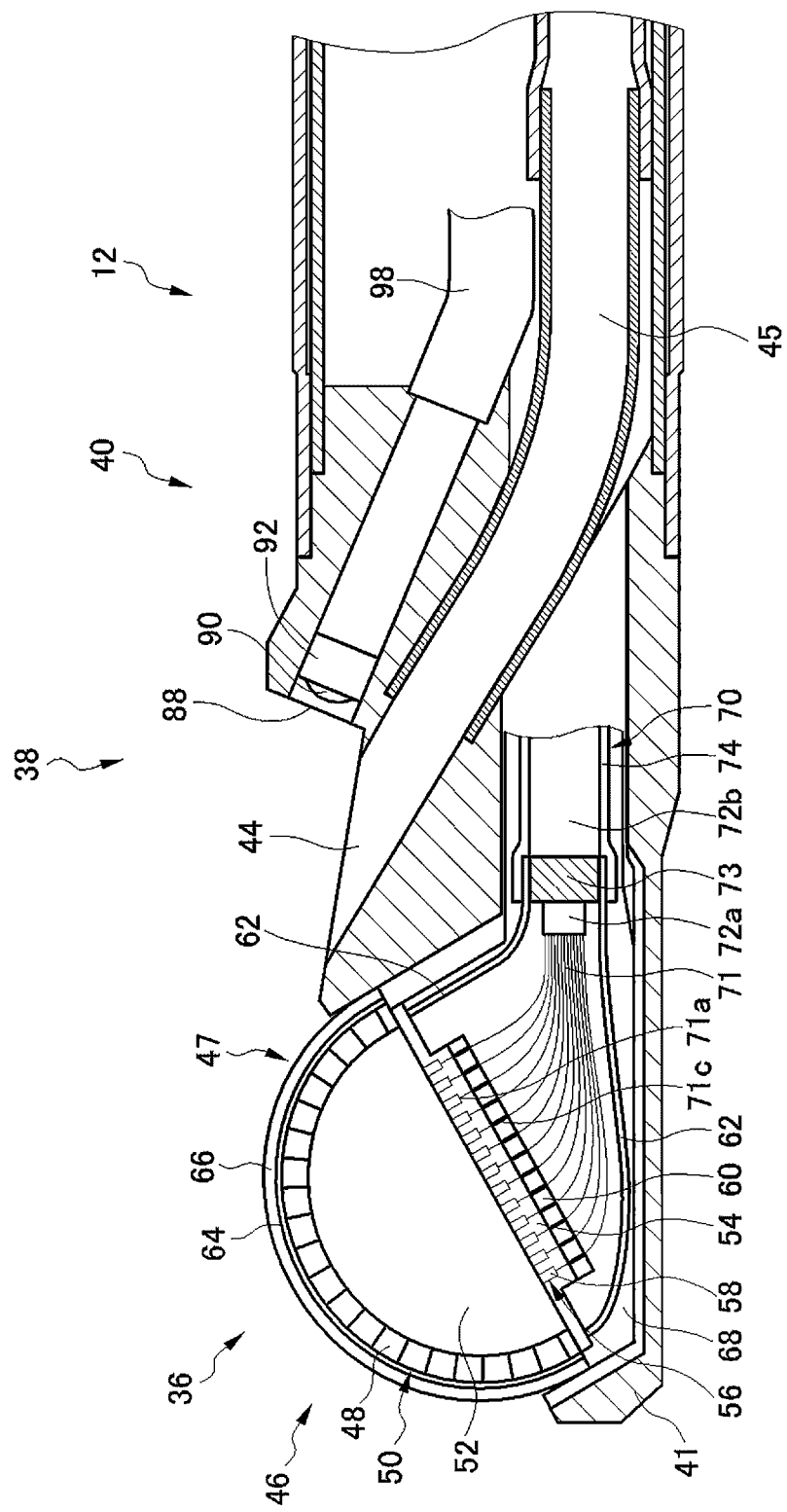
FIG. 3 is a partial longitudinal sectional view taken along line in FIG. 2, illustrating the insertion portion of the distal end portion of the ultrasonic endoscope shown in FIG. 2.

As illustrated in FIGS. 2, and 3, the distal end portion 40 of the ultrasonic endoscope 12 has the ultrasonic observation portion 36, for obtaining an ultrasound image, on the distal end side; the endoscopic observation portion 38, for obtaining an endoscopic image, on the proximal end side; and a treatment tool lead-out port 44 between these. The observation portions 36 and 38 are attached to and held by an exterior member 41 that is the body of the distal end portion 40 of the ultrasonic endoscope 12 and that is made of a rigid material such as a rigid resin.

In the example shown in FIG. 2, the treatment tool lead-out port 44 is formed between the ultrasonic observation portion 36 and the endoscopic observation portion 38. However, the present invention is not particularly limited to the example illustrated in the figure. The treatment tool lead-out port 44 may be formed in the endoscopic observation portion 38 or may be formed on the proximal end side (the bending portion 42 side) relative to the endoscopic observation portion 38.

As illustrated in FIGS. 2 and 3, the ultrasonic observation portion 36 is composed of the ultrasonic transducer unit 46, the exterior member 41 for attaching and holing the ultrasonic transducer unit 46, and a cable portion 70 that includes a plurality of coaxial cables 71 that are connected to the ultrasonic transducer unit 46.

The ultrasonic transducer unit 46 has the ultrasonic transducer array 50 that is composed of a plurality of ultrasonic transducers 48, a backing material layer 52 that supports the ultrasonic transducers 48 of the ultrasonic transducer array 50 from the lower surface side, a wiring board 54 that is embedded in the backing material layer 52 and that is electrically connected to the plurality of ultrasonic transducers 48, a copper foil 62 (first heat conductive member) that is disposed along a side surface of the backing material layer 52 in the width direction and end surfaces of the plurality of ultrasonic transducers 48 in the longitudinal direction, and a filler layer 68 that fills a space between the exterior member 41 and the backing material layer 52.

In the example shown in the figures, in the backing material layer 52, in the wiring board 54 that is electrically connected to individual electrodes (not shown) of the plurality of ultrasonic transducers 48, a wiring portion 56 that has a plurality of connection portions 58, to which signal wires 71a at one ends of the plurality of coaxial cables 71 are connected, is provided. Here, drive voltage signals to the plurality of ultrasonic transducers 48 and ultrasonic echo signals (voltage signals) from the plurality of ultrasonic transducers 48 are applied to the individual electrodes of the plurality of ultrasonic transducers 48. The plurality of coaxial cables 71 are electrically connected to the ultrasonic processor device 14 at the other ends thereof. The signal wires 71a of the plurality of coaxial cables 71 are each electrically connected to a corresponding one of the plurality of ultrasonic transducers 48. Moreover, the wiring board 54 has, in the wiring portion 56, a ground portion 60 that is electrically connected, via a lead wire or the like, to a transducer ground (not shown) that is a ground electrode of the ultrasonic transducer array 50. The ground portion 60 may be connected to shield layers 71c of the plurality of coaxial cables 71.

The ultrasonic transducer unit 46 further has an acoustic matching layer 64 that is laminated on the ultrasonic transducer array 50, and an acoustic lens 66 that is laminated on the acoustic matching layer 64. That is, the ultrasonic transducer unit 46 is composed of a laminated body 47 in which the acoustic lens 66, the acoustic matching layer 64, the ultrasonic transducer array 50, and the backing material layer 52 are laminated.

The acoustic matching layer 64 performs acoustic impedance matching between a subject, such as a human body, and the ultrasonic transducers 48.

The acoustic lens 66, which is attached onto the acoustic matching layer 64, causes ultrasound, which is emitted from the ultrasonic transducer array 50, to converge toward an observation target site. The acoustic lens 66 is made of, for example, a silicone-based resin (a millable silicone rubber (HTV rubber), a liquid silicone rubber (RTV rubber), or the like), a butadiene-based resin, a polyurethane-based resin, or the like. In order to perform acoustic impedance matching between a subject and the ultrasonic transducers 48 by using the acoustic matching layer 64 and to increase transmittance of ultrasound, powder of titanium oxide, alumina, silica, or the like is mixed into the acoustic lens 66 as necessary.

The cable portion 70 of the ultrasonic observation portion 36 has a heat dissipation structure that is the feature of the present invention. As illustrated in FIG. 4, the cable portion 70 has the plurality of coaxial cables 71 disposed on the central side, an insulating jacket 72a that covers the plurality of coaxial cables 71, an electroconductive shield member 73 that is disposed so as to cover the jacket 72a and that can be grounded to the housing of the ultrasonic endoscope 12, and a jacket 72b that covers the outside of the shield member 73. The cable portion 70 has a first insulation tube 74 for covering and protecting the outer periphery of the outer jacket 72b; an electroconductive connection pipe 76 that is disposed on the proximal end side of the cable portion 70 (a side opposite to the laminated body 47) and that covers at least a part of the first insulation tube 74; and a second insulation tube 78 that is connected to an end portion of the connection pipe 76 on a side opposite to the ultrasonic transducer unit 46 and that covers a connection portion with the connection pipe 76 and the first insulation tube 74 on the universal cord 26 side relative to the connection pipe 76. Moreover, a second heat conductive member 80 is disposed so as to fill at least a part of a space between the first insulation tube 74 and the connection pipe 76. The shield member 73 of the cable portion 70 may be made from a metal member or the like, provided that the shield member 73 covers the plurality of coaxial cables 71 from the outside and has electroconductivity. In FIG. 4, which is a figure simplified for convenience of description, only the ultrasonic transducer array 50, the backing material layer 52, the copper foil 62, the wiring board 54, and the cable portion 70 are illustrated, and other members are omitted.

Here, the meaning of "grounding" in the present invention is not limited to causing the potential of an electroconductive member to be zero, and also includes a case where, for example, the voltage of an electroconductive member is maintained at a predetermined low voltage by connecting the electroconductive member to a member having a large electric capacity.

The plurality of coaxial cables 71 are electrically connected to the plurality of connection portions 58 of the wiring portion 56 of the wiring board 54. Moreover, the shield member 73 is thermally connected to the copper foil 62 of the ultrasonic transducer unit 46 at an end portion thereof on the ultrasonic transducer unit 46 side. Therefore, in order from the end portion of the cable portion 70 on the ultrasonic transducer unit 46 side, the coaxial cables 71 and the inner jacket 72a are exposed in the ultrasonic observation portion 36. At a portion of the exposed inner jacket 72a that is adjacent to a side opposite to the ultrasonic transducer unit 46, the outer jacket 72b is removed and the shield member 73 is exposed, and the exposed shield member 73 and the copper foil 62 are connected to each other.

The ultrasonic transducer array 50 of the ultrasonic transducer unit 46 shown in FIGS. 2 and 3 is, for example, an array of 48 to 192 channels (CH) that is composed of 48 to 192 pieces of rectangular-parallelepiped-shaped ultrasonic transducers 48 that are arranged in an outwardly convex arc shape.

That is, the ultrasonic transducer array 50 is formed by arranging the plurality of ultrasonic transducers 48, for example, in a one-dimensional array shape at a predetermined pitch as in the example shown in the figures. Thus, the ultrasonic transducers 48 of the ultrasonic transducer array 50 are arranged at a regular pitch in the axial direction of the distal end portion 40 (the longitudinal axial direction of the insertion portion 22) in a convexly curved shape and are sequentially driven on the basis of drive signals that are input from the ultrasonic processor device 14. Thus, convex electronic scan is performed over a scan range that is a range in which the ultrasonic transducers 48 are arranged as shown in FIG. 2.

The length of the ultrasonic transducer array 50 in the width direction of the ultrasonic transducer array 50, that is, the longitudinal direction of the ultrasonic transducers 48 (elevation (EL) direction) is smaller than the length of the ultrasonic transducer array 50 in a direction parallel to the bottom surface of the backing material layer 52 (the azimuth (AZ) direction). The ultrasonic transducer array 50 is disposed so as to be inclined in such a way that the back end side thereof protrudes. The ultrasonic transducer 48 has a structure in which, for example, electrodes are formed on both surfaces of a thick piezoelectric film of lead zirconate titanate (PZT), polyvinylidene fluoride (PVDF), or the like. An electrode of the ultrasonic transducer array 50 is an individual electrode (not shown) that is independently provided in each ultrasonic transducer 48, and the other electrode is a transducer ground (transducer ground electrode) (not shown), which is common to all of the ultrasonic transducers 48. For example, a plurality of the individual electrodes are disposed on the lower surfaces of end portions of the plurality of ultrasonic transducers 48, and the transducer ground may be disposed on the upper surfaces of the end portions of the ultrasonic transducers 48. In this case, the plurality of individual electrodes and the transducer ground constitute an electrode portion of the ultrasonic transducer array 50.

Each gap between two adjacent ultrasonic transducers 48 is filled with a filler, such as an epoxy resin or the like.

In the ultrasonic transducer unit 46 of the ultrasonic observation portion 36, when each of the ultrasonic transducers 48 of the ultrasonic transducer array 50 is driven and a voltage is applied to both electrodes of the ultrasonic transducer 48, the piezoelectric body vibrate and successively generates ultrasound, and the ultrasound is emitted toward an observation target site of a subject. By successively driving the plurality of ultrasonic transducers 48 by using an electronic switch such as a multiplexer, ultrasound is scanned over a scan range along a curved surface on which the ultrasonic transducer array 50 is disposed, such as a range of about several tens of millimeters from the center of curvature of the curved surface.

When receiving an echo signal (ultrasonic echo) reflected from the observation target site, the piezoelectric body vibrates and generates a voltage, and this voltage is output to the ultrasonic processor device 14 as an electric signal corresponding to the received ultrasonic echo (ultrasound detection signal). The ultrasonic processor device 14 performs various types of signal processing on the electric signal, and then an ultrasound image is displayed on the monitor 20.

Heat is generated in each of piezoelectric bodies of the plurality of ultrasonic transducers 48 when, as described above, a drive voltage is applied to the plurality of ultrasonic transducers 48 and the piezoelectric bodies of the plurality of ultrasonic transducers 48 vibrate and generate ultrasound emitted toward a target object, and when the plurality of ultrasonic transducers 48 receive an ultrasonic echo of ultrasound, which has been emitted from the plurality of ultrasonic transducers 48 and reflected by the target, and the piezoelectric bodies vibrates and generate an ultrasonic echo signal (voltage signal). One of means for increasing the resolution of an ultrasound image, that is, for improving accuracy in ultrasonic diagnosis is means of increasing the power of drive signals (voltage signals) of the plurality of ultrasonic transducers 48. However, as the drive voltage increases, heat generated in the piezoelectric body increases. Therefore, by providing a heat dissipation structure that is a feature of the present invention in the distal end portion 40 of the ultrasonic endoscope 12, it is possible to efficiently dissipate heat generated in the piezoelectric body and to improve accuracy in ultrasonic diagnosis.

Although not illustrated, the ultrasonic transducer array 50 has a plurality of (48 to 192) electrodes (not shown) that are electrically continuous with the plurality of (48 to 192) ultrasonic transducers 48. The plurality of electrodes that are electrically continuous with the plurality of ultrasonic transducers 48 may be disposed on a side surface of the ultrasonic transducer array 50 in the width direction, or may be on the central side of the ultrasonic transducer array 50 as in the present embodiment. In a case where the plurality of electrodes that are electrically continuous with the ultrasonic transducers 48 are disposed on the side surface side of the ultrasonic transducer array 50 in the width direction, if the number of the ultrasonic transducers 48 is small, the plurality of electrodes may be disposed on one surface side. However, in order to improve the accuracy in ultrasonic diagnosis, preferably, the number of the ultrasonic transducers 48 is large. Therefore, preferably, the plurality of electrodes that are electrically continuous with the ultrasonic transducers 48 are disposed on both surface sides of the ultrasonic transducer array 50 in the width direction. As in the present embodiment, in a case where the plurality of electrodes that are electrically continuous with the plurality of ultrasonic transducers 48 are disposed on the central side of the ultrasonic transducer array 50 in the width direction, because the wiring portion can be disposed in the backing material layer 52, the space in the distal end portion 40 of the insertion portion 22 is not squeezed. Therefore, even in a case where, for example, the ultrasonic transducers 48 are arranged in multiple rows, the space in the distal end portion 40 can be effectively used.

Moreover, although not illustrated, the transducer ground (not shown) of the plurality of ultrasonic transducers 48 is an electrode that is different from the plurality of electrodes (not shown) that are disposed on the central side of the ultrasonic transducer array 50 in the width direction. The transducer ground is electrically connected to the ground portion 60 of the wiring portion 56 of the wiring board 54, which is a grounded member, by using a lead wire or the like. Moreover, because the ground potential in the ultrasonic endoscope 12 is preferably the same reference potential, preferably, the transducer ground of the plurality of ultrasonic transducers 48 is a common electrode to which the ultrasonic transducers 48 are grounded.

Next, as shown in FIG. 3, the backing material layer 52 of the ultrasonic transducer unit 46 is a layer that is made of a backing material and that is disposed inside with respect to the arrangement surface of the plurality of ultrasonic transducers 48, that is, on the back surface (lower surface) of the ultrasonic transducer array 50. Accordingly, the backing material layer 52 has a function of mechanically and softly supporting the ultrasonic transducer array 50 and a function of attenuating, among ultrasound signals emitted from the plurality of ultrasonic transducers 48 or reflected and propagated from an observation target, ultrasound that has propagated to the backing material layer 52 side. Therefore, the backing material is a material having rigidity, such as a rigid rubber, to which an ultrasound attenuation material (such as ferrite or a ceramic) is added as necessary.

Accordingly, preferably, the ultrasonic transducer array 50 is an array in which the plurality of ultrasonic transducers 48 each having a rectangular-parallelepiped shape in the example shown in the figures are arranged at a regular pitch on the arc-shaped upper surface of the backing material layer 52, which is an upper surface having a convex arc-shaped cross section, in such a way that the longitudinal directions of the plurality of ultrasonic transducers 48 are parallel to each other, that is, an array in which the plurality of ultrasonic transducers 48 are arranged in an arc shape so as to face outward.

The shape of the backing material layer 52 may be any appropriate shape that does not impair the functions described above. The backing material layer 52 may have a substantially semi-cylindrical shape shown in FIG. 3, and may have a recessed portion.

The filler layer 68 of the ultrasonic transducer unit 46 fills a space between the exterior member 41 and the backing material layer 52. The filler layer 68 also has a function of fixing the wiring board 54, the plurality of coaxial cables 71, the copper foil 62, and various wiring portions. Preferably, the acoustic impedance of the filler layer 68 matches the acoustic impedance of the backing material layer 52 with an accuracy of a predetermined degree or higher so that a boundary surface between the filler layer 68 and the backing material layer 52 may not reflect an ultrasound signal propagated from the ultrasonic transducer array 50 toward the backing material layer 52 side. Moreover, preferably, the filler layer 68 has heat dissipation ability in order to increase the efficiency in dissipating heat generated in the plurality of ultrasonic transducers 48. When the filler layer 68 has heat dissipation ability, because heat is received from the backing material layer 52, the wiring board 54, the copper foil 62, and the plurality of coaxial cables 71, heat dissipation efficiency can be improved.

As illustrated in FIG. 3, a part of the wiring board 54 of the ultrasonic transducer unit 46 is embedded in the backing material layer 52. The wiring board 54 has, in a portion thereof embedded in the backing material layer 52, a plurality of electrodes (not shown) that are electrically continuous with the plurality of ultrasonic transducers 48, a plurality of electrode pads (not shown) that are electrically connected by using lead wires or the like, the wiring portion 56 that is composed of the plurality of connection portions 58 that are terminals connected to the signal wires 71a of the plurality of coaxial cables 71 of the cable portion 70, and the ground portion 60 that is electrically connected to the transducer ground (not shown) of the plurality of ultrasonic transducers 48. The wiring board 54 may be a board made of a rigid material, or may be a flexible printed circuit (hereinafter, simply referred to as "FPC"). As in the present embodiment, in a case where a part of the wiring board 54 is embedded in the backing material layer 52, preferably, the wiring board 54 is made of a rigid material in order to fix the position of the wiring portion 56 and to prevent wire breakage at the wiring portion. For example, in a case where a plurality of electrodes that are electrically continuous with the plurality of ultrasonic transducers 48 are disposed on a side surface of the ultrasonic transducer array 50 in the width direction and the wiring board 54 is disposed along a side surface of the backing material layer 52 in the width direction, preferably, an FPC is used as the wiring board 54 in order to, for example, improve the operational efficiency of wiring.

The copper foil 62 of the ultrasonic transducer unit 46 is affixed along the side surfaces of the ultrasonic transducer array 50 and the backing material layer 52 in the width direction. The copper foil 62 conducts heat generated in the plurality of ultrasonic transducers 48. As illustrated in FIGS. 3 and 4, at least a part of the copper foil 62 is extended to the shield member 73 of the cable portion 70 and is thermally connected to the shield member 73. By thermally connecting the copper foil 62 and the shield member 73 in this way, heat generated in the plurality of ultrasonic transducers 48 can be dissipated to the electroconductive shield member 73 that covers the plurality of coaxial cables 71 from the outside. Moreover, because the shield member 73 is an electroconductive member, in a case where the shield member 73 is grounded to the housing of the ultrasonic endoscope 12 or the like at a proximal end portion thereof opposite to the distal end portion 40 of the insertion portion 22, the potential of the copper foil 62 can be made to be the ground potential. Therefore, the copper foil 62 can be prevented from electromagnetically interfering with ultrasonic echo signals (voltage signals) obtained from the plurality of ultrasonic transducers 48.

In order to make the potential of the copper foil 62 be the ground potential, the copper foil 62 may be connected to the ground portion 60 of the wiring board 54. Preferably, the copper foil 62 used in the present embodiment is an electroconductive member for the above reasons. However, in view of heat dissipation, the copper foil 62 may be any member having high heat conductivity. Therefore, instead of the copper foil 62, an aluminum foil, an electroconductive silicone sheet, or the like may be used.

Moreover, the shape of the copper foil 62 is not limited to a foil shape. Preferably, the copper foil 62 has a mesh shape or a sheet shape that is thicker than a foil so that the copper foil 62 can sufficiently conduct heat from the side surfaces of the ultrasonic transducer array 50 and the backing material layer 52 in the width direction. A portion of the copper foil 62 that is affixed along the outer surfaces of the ultrasonic transducer array 50 and the backing material layer 52 and a portion of the copper foil 62 that is extended to the shield member 73 of the cable portion 70 need not be integrated. In this case, the shape of the portion that is extended to the shield member 73 is not limited to a shape that is the same as the shape of the portion affixed to the side surface of the backing material layer 52, such as a mesh shape or a sheet shape, and may be another shape, such as a lead-wire shape, a bar-like shape, or the like. Moreover, the material of the portion disposed along the backing material layer 52 and the material of the portion that is extended to the shield member 73 may be different from each other.

The wiring portion 56 of the wiring board 54 is composed of the connection portions 58, which are a plurality of terminals that are disposed on at least one surface of the wiring board 54, that are electrically connected to the signal wires 71a of the plurality of coaxial cables 71 of the cable portion 70, and that are electrically connected to a plurality of electrode pads (not shown) that are electrically continuous with the plurality of ultrasonic transducers 48. In the examples shown in FIGS. 3, 4, and 6 to 8, the wiring portion 56 is disposed on the backing material layer 52 side relative to the ground portion 60 of the wiring board 54. The position of the wiring portion 56 is not particularly limited. The wiring portion 56 may be disposed at any appropriate position in order to, for example, improve the operation efficiency in wiring. Preferably, the number of the plurality of connection portions 58 of the wiring portion 56 is at least equal to the number of channels of the ultrasonic transducer array 50. Therefore, as necessary, the plurality of connection portions 58 may be disposed on the wiring board 54 in multiple rows.

The ground portion 60 of the wiring board 54 is an electroconductive member that is connected to the transducer ground of the plurality of ultrasonic transducers 48 (not shown) and to the shield layers 71c of the plurality of coaxial cables 71. In a case where the shield layers 71c of the plurality of coaxial cables 71 are grounded, the ground portion 60 makes the ground potentials of the shield layers 71c of the plurality of coaxial cables 71 be the same potential. Therefore, for example, in order to increase the number of heat dissipation paths from the plurality of ultrasonic transducers 48, the ground portion 60 may be further electrically connected to the shield member 73 of the cable portion 70.

Figure 4:
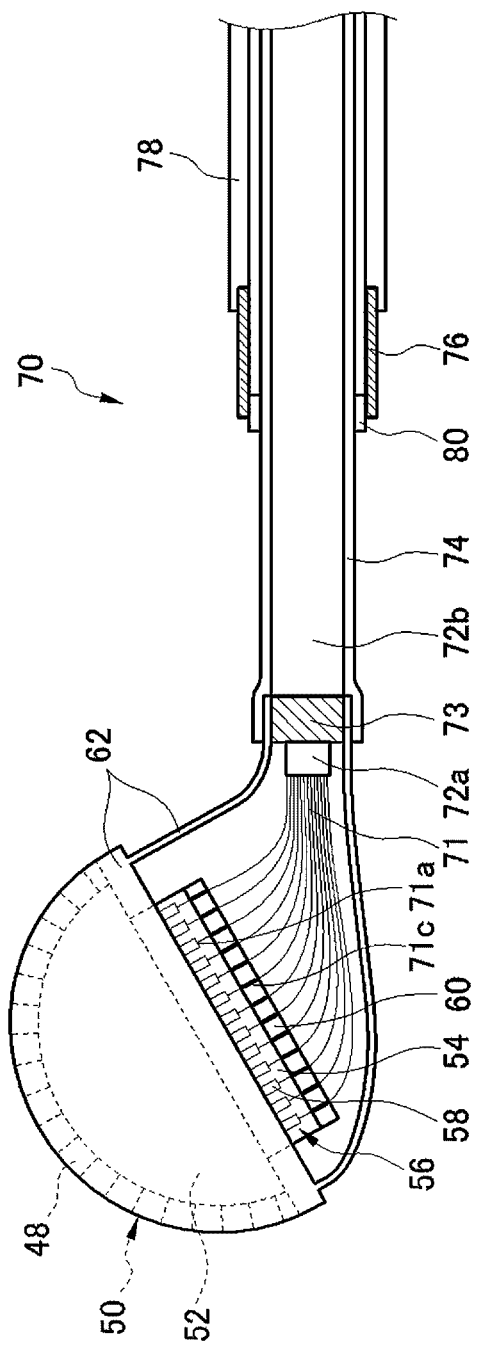
FIG. 4 is a schematic partial longitudinal sectional view of the distal end portion of the insertion portion of the ultrasonic endoscope shown in FIGS. 1 to 3.
Figure 5:
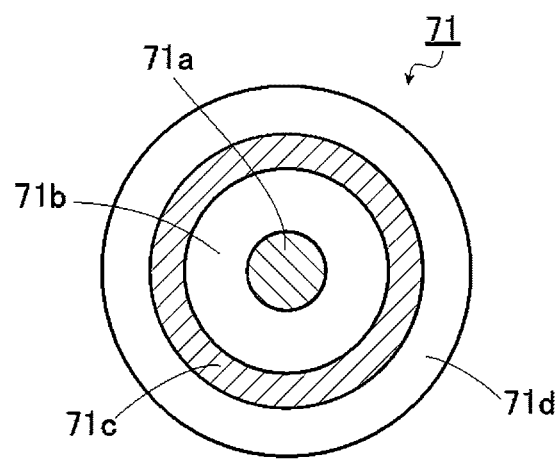
FIG. 5 is a schematic cross-sectional view of a coaxial cable of a cable portion shown in FIGS. 3 and 4.

As illustrated in FIG. 5, each of the plurality of coaxial cables 71 of the cable portion 70 has a signal wire 71a that is on the central side thereof and that is electrically connected to a corresponding one of the plurality of connection portions 58 of the wiring portion 56 of the wiring board 54; an insulating jacket 71b that is disposed in a layer outside of the signal wire 71a; a shield layer 71c that is disposed in a layer outside of the jacket 71b, that can be grounded on the proximal end side (the universal cord 26 side) of the ultrasonic endoscope 12, and that is made of an electroconductive material such as a metal; and an insulating jacket 71d that is disposed in the outermost layer. Therefore, as in the examples shown in FIGS. 3, 4, and 6 to 8, in the case where the wiring portion 56 is disposed on the wiring board 54 at a position on the backing material layer 52 side relative to the ground portion 60, it is possible to wire the signal wires 71a of the plurality of coaxial cables 71 to the wiring portion 56 in such a way that the plurality of coaxial cables 71 are not bent.

In the example shown in FIG. 4, the plurality of coaxial cables 71 are used on the central side of the cable portion 70. However, cables (shield cables) that have structures different from the coaxial cables 71 described above may be used, provided that the cables each have a signal wire, for transmitting/receiving a voltage signal by being electrically connected to a corresponding one of the plurality of ultrasonic transducers 48, and a shield portion that is made of a metal and that can be grounded by being electrically connected to a transducer ground (not shown) of a corresponding one of the plurality of ultrasonic transducers 48. For example, although not illustrated, as the shield cable, it is possible to use a cable having a known structure, such as a cable unit that includes, on the central side thereof, a plurality of signal wires covered by an insulating jacket and a plurality of lead wires that can be grounded; and has a jacket that covers the plurality of signal wires and the lead wires. The arrangement of the signal wires and the lead wires of the cable unit is not limited to the one described above. The plurality of signal wires and lead wires may be randomly arranged in the outer jacket that covers these wires.

As illustrated in FIG. 4, the first insulation tube 74 of the cable portion 70 is an insulating tube for covering and protecting the plurality of coaxial cables 71, the inner jacket 72a, and the shield member 73. Therefore, the first insulation tube 74 is disposed so as to cover the shield member 73, which is exposed by removing the outer jacket 72b in order to connect the copper foil 62. Here, the first insulation tube 74 is not particularly limited, provided that the first insulation tube 74 has a certain degree of flexibility and insulation ability for following a bending operation of bending the bending portion 42 of the insertion portion 22 and for protecting the plurality of coaxial cables 71, the shield member 73, and the connection portion between the shield member 73 and the copper foil 62. A known insulation tube, such as a heat shrinkable tube, may be used.

The connection pipe 76 of the cable portion 70 is a member for dissipating heat that is conducted from the shield member 73 by contacting the second heat conductive member 80. Preferably, the connection pipe 76 covers a portion of the first insulation tube 74 having a predetermined length and is disposed on the operating unit 24 side (proximal end side) relative to the distal end portion 40 so as not to dissipate heat into the distal end portion 40 of the insertion portion 22. The length of the connection pipe 76 may be a length that does not impede a bending operation of the bending portion 42, and preferably is as large as possible in order to maintain heat dissipation ability. Moreover, in order to efficiently dissipate heat conducted from the shield member 73, preferably, the connection pipe 76 is made of a material having high heat conductivity, such as a stainless steel or another metal.

The second insulation tube 78 of the cable portion 70, which covers the first insulation tube 74, protects the cable portion 70 from the outside and fixes the connection pipe 76 at a position outside the first insulation tube 74. An end portion of the second insulation tube 78 on the ultrasonic transducer unit 46 side (distal end side) is connected to an end of the connection pipe 76 on a side opposite to the ultrasonic transducer unit 46 (proximal end side). At this time, the second insulation tube 78 is disposed on the proximal end side of the ultrasonic endoscope 12 so as to cover a part of the connection pipe 76 on the proximal end side and a part of the first insulation tube 74, that is, a part on the proximal end side relative to the connection pipe 76.

As with the first insulation tube 74, the second insulation tube 78 is not particularly limited, provided that the second insulation tube 78 has a certain degree of flexibility and insulation ability. A known insulation tube, such as a heat shrinkable tube, may be used.

The second heat conductive member of the cable portion 70 is disposed in contact with the first insulation tube 74 and the connection pipe 76 and conducts heat, which has been conducted to the shield member 73, to the connection pipe 76. In the example shown in FIG. 4, the second heat conductive member 80 is a cylindrical member that is disposed between the first insulation tube 74 and the connection pipe 76 on the distal end side of the connection pipe 76. As in the example shown in FIG. 4, the second heat conductive member 80 may conduct heat from the shield member 73 via the outer jacket 72b and the first insulation tube 74 of the cable portion 70. Therefore, preferably, the second heat conductive member 80 has high heat conductivity. Preferably, the second heat conductive member 80 is made of a metal such as copper or aluminum, a ceramic having high heat conductivity, heat conductive silicone, or the like.

In order to sufficiently conduct heat from the shield member 73, preferably, the second heat conductive member 80 is disposed so as to fill at least a part of a space between the first insulation tube 74 and the connection pipe 76. Therefore, the second heat conductive member 80 need not have a cylindrical shape as in the example shown in FIG. 4.

A heat conductive member having any appropriate shape, such as a sheet shape or a mesh shape, may be used. In order to increase the heat transfer efficiency from the shield member 73, preferably, the second heat conductive member 80 is disposed in contact with the first insulation tube 74 and the connection pipe 76 over as large area as possible. For example, the second heat conductive member 80 may be disposed so as to fill the entirety of a space between the first insulation tube 74 and the connection pipe 76. Moreover, preferably, the second heat conductive member 80 is disposed in such a way that the second heat conductive member 80 can be easily removed for repair or the like. For example, the second heat conductive member 80 may be disposed so as to protrude slightly from the distal end of the connection pipe 76.

By disposing the second heat conductive member 80 in contact with the first insulation tube 74 and the connection pipe 76 as described above, heat generated in the plurality of ultrasonic transducers 48 can be conducted to the shield member 73 and connection pipe 76 of the cable portion 70. As a result, in addition to the shield member 73, a heat dissipation path to the connection pipe 76 can be formed, and the heat dissipation efficiency in the ultrasonic observation portion 36 of the distal end portion 40 is improved.

Figure 6:
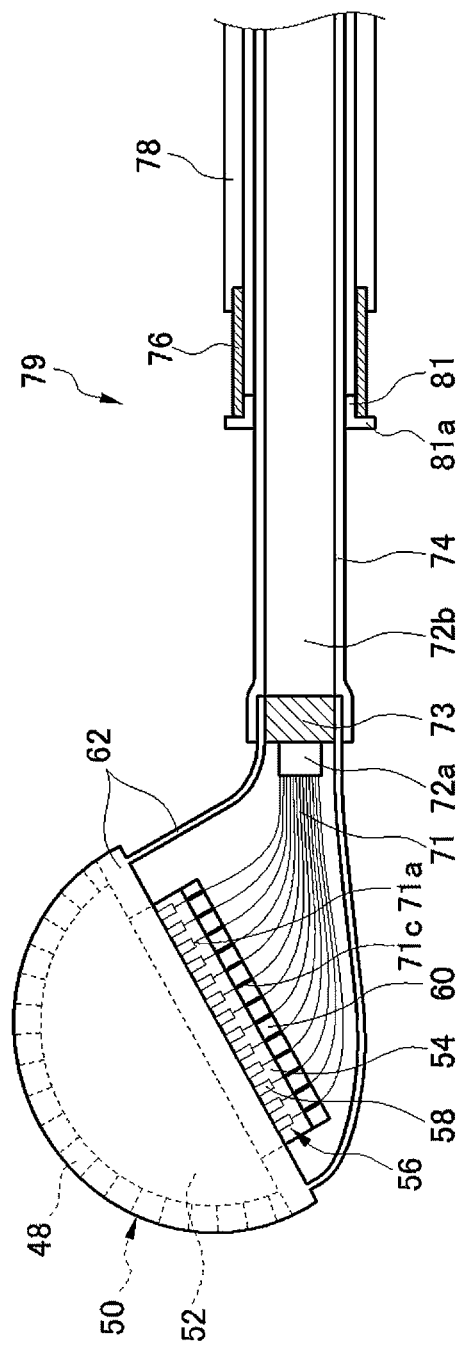
FIG. 6 is a partial longitudinal sectional view of another example of a distal end portion of an insertion portion of an ultrasonic endoscope according to a first embodiment of the present invention.

In another example shown in FIG. 6, a second heat conductive member 81 includes a cylindrical portion that is disposed between the first insulation tube 74 and the connection pipe 76 and an outward flange 81a that has a cylindrical shape having an outside diameter that is larger than or equal to the inside diameter of the connection pipe 76. As illustrated in FIG. 6, preferably, the second heat conductive member 81 is disposed in such a way that the outward flange 81a contacts an end surface of the connection pipe 76 on the distal end side. In this case, because the second heat conductive member 81 is in contact with, in addition to a space between the first insulation tube 74 and the connection pipe 76, the end surface of the connection pipe 76 on the distal end side, the heat dissipation path to the connection pipe 76 can be widened. Because the outward flange 81a contacts the end surface of the connection pipe 76 on the distal end side, it is possible to prevent the connection pipe 76 from moving toward the distal end side relative to the first insulation tube 74 and the second heat conductive member 81, which may occur due to, for example, vibration during use of the ultrasonic endoscope 12. Moreover, because the outward flange 81a, which has an outside diameter that is larger than the inside diameter of the connection pipe 76, is located on the distal end side relative to the connection pipe 76, when performing reassembling after removing the second heat conductive member 81 for repair or the like, the insertion position of the second heat conductive member 81 can be easily determined.

In FIG. 6, which is a figure that is simplified for convenience of description as with FIG. 4, only the ultrasonic transducer array 50, the backing material layer 52, the copper foil 62, the wiring board 54, and a cable portion 79 are illustrated, and the other members is omitted.

As described above, in the example shown in FIG. 6, a structure in which the second heat conductive member 81 has the outward flange 81a on the distal end side has been described. However, the second heat conductive member 81 is not limited to a member that has a cylindrical shape, provided that the second heat conductive member 81 can contact at least a space between the first insulation tube 74 and the connection pipe 76 and an end portion of the connection pipe 76 on the distal end side. That is, it is sufficient that the second heat conductive member 81 shown in FIG. 6 has a thick portion (not shown), which is thicker than a portion thereof disposed between the first insulation tube 74 and the connection pipe 76, on the distal end side of the ultrasonic endoscope 12, and the thick portion is disposed in contact with the end surface of the connection pipe 76 on the distal end side of (the copper foil 62 side). The thick portion has the same effect as the outward flange 81a in FIG. 6. Moreover, the second heat conductive member 81 may be disposed so as to fill at least a part of a space between the first insulation tube 74 and the connection pipe 76. Accordingly, in this case, as in the example shown in FIG. 6, the heat dissipation path to the connection pipe 76 can be widened, and it is possible to prevent a portion of the cable portion 79 inside of the connection pipe 76 from moving toward the proximal end side and the distal end side relative to the connection pipe 76.

Here, in the examples shown in FIGS. 3, 4, and 6 to 8, the second heat conductive members 80 and 81 conduct heat from the shield members 73 via the outer jackets 72b and the first insulation tubes 74 of the cable portions 70 and 79. The outer jackets 72b and the first insulation tubes 74 of the cable portions 70 and 79, which have low heat conductivity, impede efficient dissipation of heat that is conducted to the shield members 73. Therefore, in order to improve efficiency in dissipating heat that is conducted to the shield members 73, preferably, the shield members 73 are in direct contact with the second heat conductive members 80 and 81.

Figure 7:
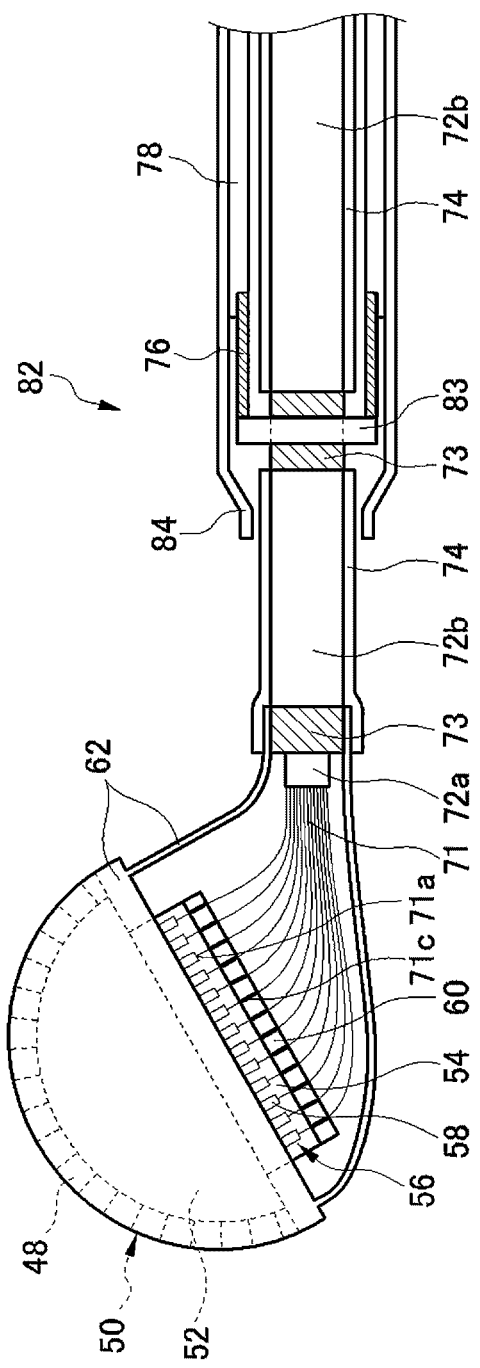
FIG. 7 is a partial longitudinal sectional view of another example of the distal end portion of the insertion portion of the ultrasonic endoscope according to the first embodiment of the present invention.

In an example of the present embodiment shown in FIG. 7, a part of the outer jacket 72b of a cable portion 82 on the distal end side of the connection pipe 76 is removed, and the shield member 73 is exposed. At the portion where the shield member 73 is exposed, a part of the first insulation tube 74 is removed, and the shield member 73 is exposed to the outside. Moreover, a second heat conductive member 83 having a cylindrical shape is disposed in such a way that the second heat conductive member 83 contacts the portion where the shield member 73 is exposed to the outside, covers the portion where the first insulation tube 74 is removed, and contacts the distal end side of the connection pipe 76. In this case, in particular, in a case where the shield layers 71c of the plurality of coaxial cables 71 and the shield member 73 of the cable portion 70 are electrically connected to each other on the proximal end side of the cable portion 70 or the like, the shield member 73 that is electrically continuous with the transducer ground (not shown) of electrode portion (not shown), which is the ground electrode of the ultrasonic transducer unit 46, is exposed to the outside. Accordingly, in the example shown in the figures, in order to insulate the shield member 73 from a structure in the ultrasonic endoscope 12, an insulating layer 84 that covers the exposed shield member 73, the second heat conductive member 83, the connection pipe 76, and the second insulation tube 78 is disposed outside of the connection pipe 76.

In FIG. 7, which is a figure that is simplified for convenience of description as with FIGS. 4 and 6, only the ultrasonic transducer array 50, the backing material layer 52, the copper foil 62, the wiring board 54, and the cable portion 82 are illustrated, and the other members are omitted.

In FIG. 7, the shape of the second heat conductive member 83 is not particularly limited, provided that the second heat conductive member 83 can contact the shield member 73 and the connection pipe 76 of the cable portion 82. A heat conductive member having any appropriate shape described above may be used. For example, in order that the heat conductive member can be removed easily when, for example, repairing the distal end portion 40 of the insertion portion 22, a heat conductive member having a C-shape, which is the shape of a cylinder from which a part of an arc is cut away, may be used. Regarding the insulating layer 84, which is disposed outside of the connection pipe 76, it is sufficient that the insulating layer 84 is disposed so as to cover at least the exposed portion the shield member 73. Provided that the insulating layer 84 has insulating property, a known insulation tube, such as a heat shrinkable tube or the like, can be used as the insulating layer 84.

Increasing the heat dissipation paths is one of means for efficiently dissipating heat that is generated in the plurality of ultrasonic transducers 48 and conducted to the shield members 73 of the cable portions 70, 79, and 82 shown in FIGS. 3, 4, 6, and 7. In an example of the present embodiment shown in FIG. 8, a third heat conductive member 86, which fills a space between the first insulation tube 74, and a portion of the connection pipe 76 on the proximal end side and the second insulation tube 78, is provided. The third heat conductive member 86 extends from the proximal end side of the connection pipe 76 to the proximal end side of a cable portion 85. Therefore, the third heat conductive member 86 conducts both of heat that is conducted from the shield member 73 of the cable portion 85 through the second heat conductive member 80 and the connection pipe 76, and heat that is conducted from the shield member 73 through the outer jacket 72b of the cable portion 85 and the first insulation tube 74; and dissipates the both to the proximal end side. Accordingly, the ultrasonic endoscope 12 has, in addition to the heat dissipation path that dissipates heat to the proximal end side of the shield member 73 and the heat dissipation path that dissipates heat from the connection pipe 76 to the outside, a heat dissipation path to the proximal end side of the third heat conductive member 86. Therefore, the ultrasonic endoscope 12 can further improve heat dissipation efficiency.

Figure 8:
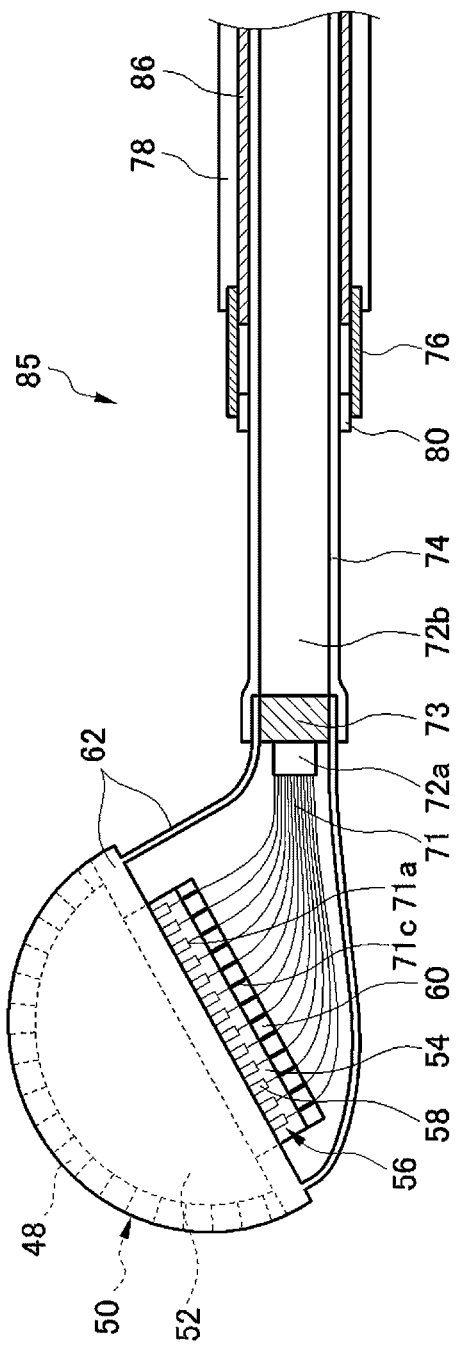
FIG. 8 is a partial longitudinal sectional view of another example of the distal end portion of the insertion portion of the ultrasonic endoscope according to the first embodiment of the present invention.

In FIG. 8, which is a figure that is simplified for convenience of description as with FIGS. 4, 6, and 7, only the ultrasonic transducer array 50, the backing material layer 52, the wiring board 54, the copper foil 62, and the cable portion 85 are illustrated, and the other elements are omitted.

As described above, in order to improve heat dissipation efficiency, preferably, the third heat conductive member 86 of the cable portion 85 extends to the proximal end side of the cable portion 85 relative to the connection pipe 76 between the first insulation tube 74 and the second insulation tube 78. Therefore, for ease of disposition and the like, the third heat conductive member 86 is formed as a heat conductive layer on the surface of the first insulation tube 74. Thus, in the case where the third heat conductive member 86 is disposed as a heat conductive layer, by using means such as application or electroless plating, at least in a portion that contacts the connection pipe 76, and preferably, on the proximal end side of the cable portion 85 relative to the second heat conductive member 80, the heat conductive layer can be formed on the surface of the first insulation tube 74. Preferably, the third heat conductive member 86, which is disposed as a heat conductive layer, is made of a material that has high heat conductivity and that has flexibility that allows the third heat conductive member 86 to follow a bending operation of bending the bending portion 42. For example, as means for forming heat conductive layer, epoxy adhesive 122-07 made by Creative Materials Inc., heat conductive grease X-23-8033-1 made by Shin-Etsu Silicones Co., Ltd., or, in a case of using electroless plating, copper or the like may be used.

As described above, as the third heat conductive member 86, a heat conductive layer formed on the first insulation tube 74 is preferably used. However, a heat conductive member may be formed on an inner wall of the connection pipe 76 and an inner wall of the second insulation tube 78, provided that the heat conductive member contacts the first insulation tube 74 and the connection pipe 76 and extends to the proximal end of the cable portion 85. The third heat conductive member 86 need not disposed as a layer and may have a mesh shape, a sheet shape, or the like. Moreover, the third heat conductive member 86 need not be disposed over the entire area where the second insulation tube 78 covers the first insulation tube 74. In accordance with the structure of the ultrasonic endoscope 12 and the like, the third heat conductive member 86 may be partially disposed or may contact the second heat conductive member 80.

With the structure of the distal end portion 40 of the insertion portion 22 of the ultrasonic endoscopes 12 shown in FIGS. 1 to 8, heat generated from the plurality of ultrasonic transducers 48 of the ultrasonic transducer array 50 can be conducted to the copper foil 62, which is a heat conductive member; and the heat can be dissipated from the copper foil 62 to the shield members 73 of the cable portions 70, 79, 82, and 85. In a case where the shield member 73 is grounded, because the copper foil 62 also has a ground potential, the copper foil 62 and the plurality of ultrasonic transducers 48 do not electromagnetically interfere with each other, and noise received from the outside can be prevented from being included in ultrasonic echoes. Moreover, because heat can be dissipated via the second heat conductive member 80, 81, and 83 to the connection pipe 76 and heat can be dissipated via the third heat conductive member 86 to the proximal end side of the cable portions 70, 79, 82, and 85, the structure has a plurality of heat dissipation paths and therefore heat dissipation efficiency can be improved. Moreover, each of the heat dissipation structures described above is a simple structure and does not occupy a large space in the distal end portion 40 of the ultrasonic endoscope 12. Accordingly, the heat dissipation structures can efficiently dissipate heat while maintaining the small size of the distal end portion 40.

In the present embodiment, the heat dissipation structures of the convex-type ultrasonic endoscope 12 have been described. However, the heat dissipation structures described above does not depend on the shape of the ultrasonic endoscope, and, as a matter of course, can be used for an ultrasonic endoscope having another shape, such as a radial type.

The endoscopic observation portion 38 is composed of an observation window 88, an objective lens 90, a solid-state imaging element 92, illumination windows 94, a cleaning nozzle 96, a wiring cable 98 composed of a plurality of coaxial cables (not shown) or the like, and the like.

The observation window 88 is attached so as to be face diagonally upward from the distal end portion 40. Reflected light from an observation target site that has entered from the observation window 88 is focused by the objective lens 90 on an imaging surface of the solid-state imaging element 92. The solid-state imaging element 92 performs photoelectric conversion of the reflected light from the observation target site, which has passed through the observation window 88 and the objective lens 90 and has been focused on the imaging surface, and outputs a captured image signal. Examples of the solid-state imaging element 92 include a charge coupled device (CCD) and a complementary metal oxide semiconductor (CMOS). The captured image signal, which has been output from the solid-state imaging element 92, passes through the wiring cable 98, which extends from the insertion portion 22 to the operating unit 24, and is transmitted to the endoscope processor device 16 via the universal cord 26. The endoscope processor device 16 performs various types of signal processing and image processing on the transmitted captured image signal and displays an endoscopic optical image on the monitor 20.

The illumination windows 94 are disposed on both sides of the observation window 88. To each of the illumination windows 94, an emission end of a light guide (not shown) is connected. The light guide extends from the insertion portion 22 to the operating unit 24, and an input end thereof is connected to the light source device 18, which is connected via the universal cord 26. Illumination light that is emitted by the light source device 18 passes through the light guide emitted from the illumination window 94 toward observation target site.

In order to clean the surfaces of the observation window 88 and the illumination windows 94, the cleaning nozzle 96 ejects air or cleaning water toward the observation window 88 and the illumination windows 94 from the water supply tank 21a and the air/water supply pipe line in the ultrasonic endoscope 12.

The distal end portion 40 has the treatment tool lead-out port 44. The treatment tool lead-out port 44 is connected to a treatment tool channel 45 that is inserted into the insertion portion 22, and a treatment tool that is inserted into the treatment tool insertion port 30 is introduced from the treatment tool lead-out port 44 into a body cavity via the treatment tool channel 45. The treatment tool lead-out port 44 is located between the ultrasonic observation portion 36 and the endoscopic observation portion 38. In a case of forming a structure that allows a treatment tool that is introduced into a body cavity to be visually checked by using an ultrasonic image, preferably, the treatment tool lead-out port 44 is disposed near the ultrasonic observation portion 36.

Although not illustrated, a stand base that changes the lead-out direction of a treatment tool, which is introduced into a body cavity from the treatment tool lead-out port 44, may be disposed in the treatment tool lead-out port 44. A wire (not shown) is attached to the stand base, and, by means of an operation of pushing or pulling a stand lever (not shown) of the operating unit 24, the angle of the stand base changes, and the treatment tool is lead out in a desired direction.

When observing the inside of a body cavity by using the ultrasonic endoscope 12, first, the insertion portion 22 is inserted into the body cavity, and an observation target site is searched while observing, on the monitor 20, an endoscopic optical image obtained by the endoscopic observation portion 38.

Next, when the distal end portion 40 reaches the observation target site and an instruction for obtaining an ultrasound tomographic image is given, a drive control signal is input from the ultrasonic processor device 14 to the ultrasonic transducers 48 via the plurality of coaxial cables 71 of the cable portion 70, 79, 82, or 85 (see FIGS. 3 to 7) in the ultrasonic endoscope 12; the wiring board 54; and the plurality of electrodes (not shown) that are electrically continuous with the ultrasonic transducers 48 of the ultrasonic transducer array 50. When the drive control signal is input, predetermined voltages are applied to both electrodes of the ultrasonic transducers 48. Then, the piezoelectric bodies of the ultrasonic transducers 48 are excited, and ultrasound is emitted toward the observation target site via the acoustic lens 66.

After emitting the ultrasound, an echo signal from the observation target site is received by the ultrasonic transducers 48. Emission of the ultrasound and reception of the echo signal are repeatedly performed while sequentially switching among the ultrasonic transducers 48 that are driven by using an electronic switch such as a multiplexer. Thus, ultrasound is scanned over the observation target site. In the ultrasonic processor device 14, an ultrasound tomographic image is generated on the basis of a detection signal that is output from the ultrasonic transducers 48 after receiving the echo signal. The generated ultrasound tomographic image is displayed on the monitor 20.

Second Embodiment

Figure 9:
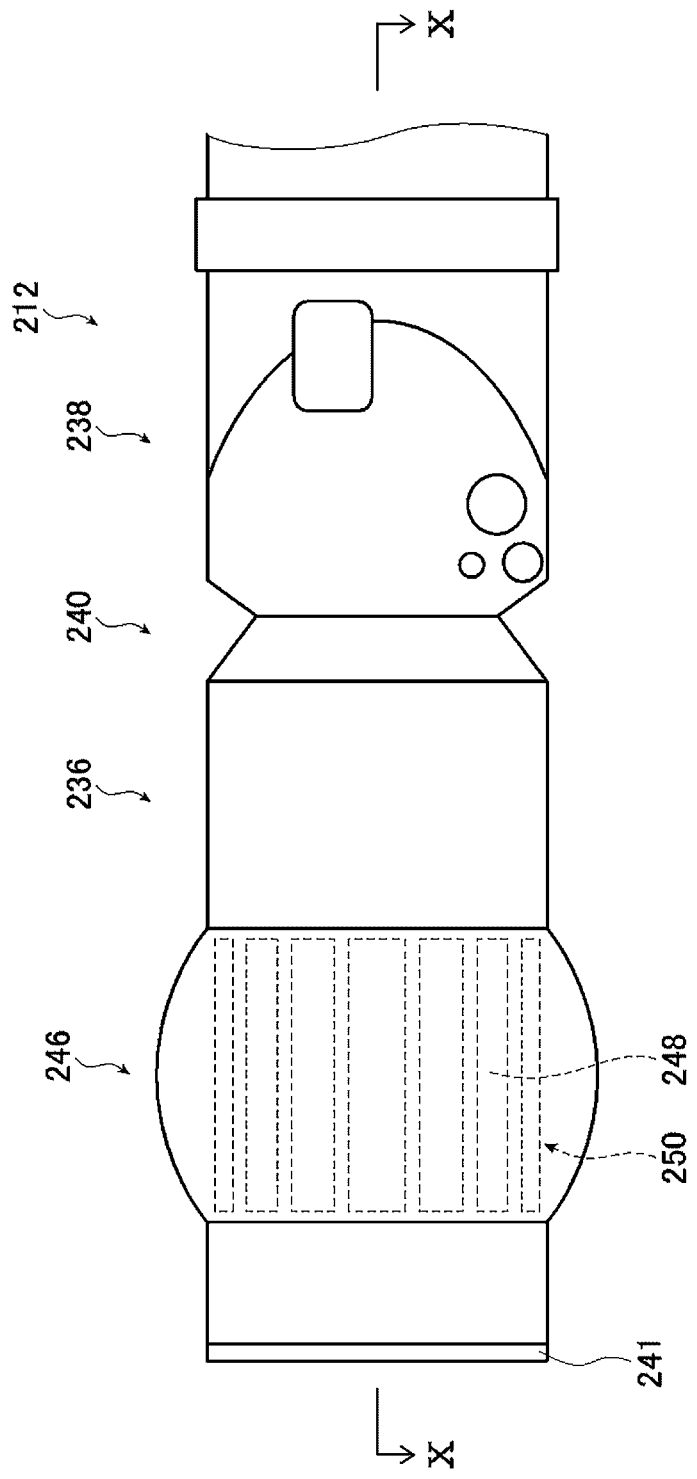
FIG. 9 is a partial enlarged plan view of a distal end portion of an insertion portion of an ultrasonic endoscope according to a second embodiment of the present invention.
Figure 10:
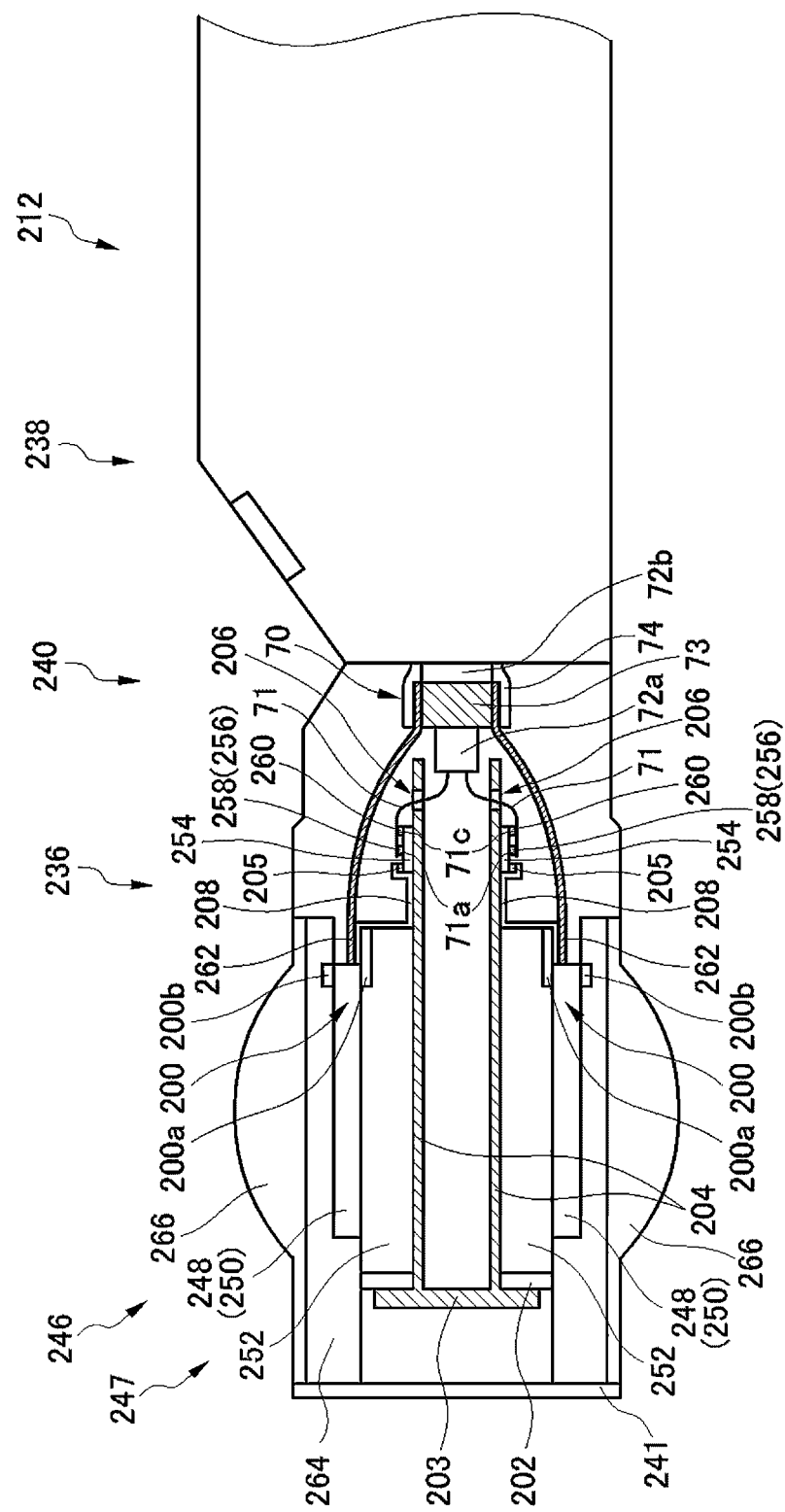
FIG. 10 is a partial longitudinal sectional view taken along line X-X in FIG. 9, illustrating the distal end portion of the ultrasonic endoscope shown in FIG. 9.

Heretofore, cases where a heat dissipation structure according to the present invention is mainly applied to a convex-type ultrasonic endoscope have been described. However, a heat dissipation structure according to the present invention can be also applied to an ultrasonic endoscope having an ultrasonic observation portion of a type other than the convex type, such as a radial type. In the present embodiment, a heat dissipation structure of a radial-type ultrasonic observation portion will be described. An ultrasonic endoscope 212 according to the present embodiment shown in FIGS. 9 and 10 differs from the ultrasonic endoscope 12 according to the first embodiment shown in FIGS. 1 to 3 in that the ultrasonic endoscope 212 includes a distal end portion 240 that includes a radial-type ultrasonic observation portion 236 and an endoscopic observation portion 238, instead of the distal end portion 40 that includes the convex-type ultrasonic observation portion 36 and the endoscopic observation portion 38. In other respects, the ultrasonic endoscope 212 has the same structure as the ultrasonic endoscope 12. In the radial-type ultrasonic observation portion 236, in particular, a member that is the same as the cable portion 70 of the first embodiment shown in FIGS. 3 and 4 is used. In FIGS. 9 and 10, the cable portion 70 is denoted by the same numerals as in FIGS. 3 and 4, and detailed description will be omitted.

Figure 11:
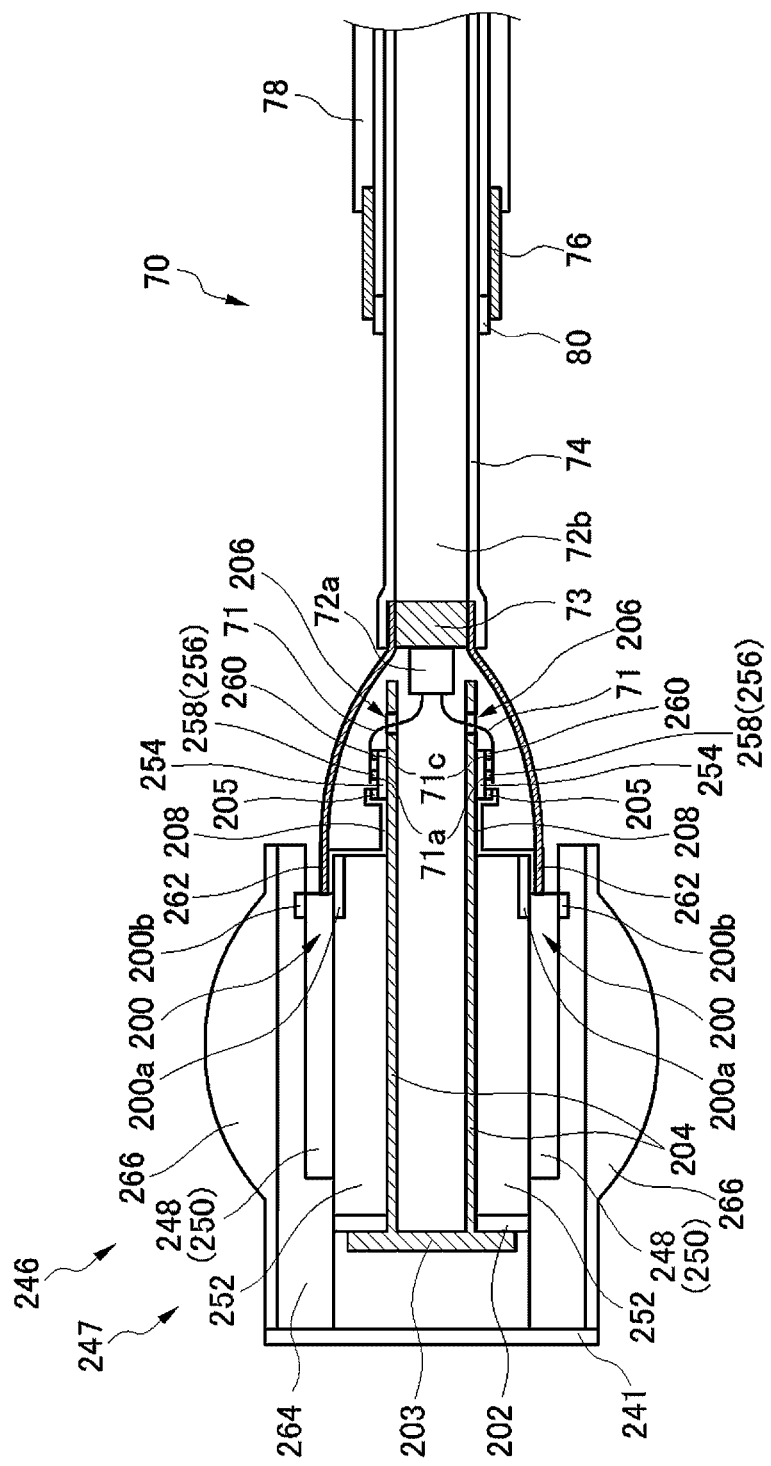
FIG. 11 is a schematic partial longitudinal sectional view of the ultrasonic endoscope shown in FIGS. 9 and 10.

FIG. 9 is a partial enlarged plan view of a distal end portion of an insertion portion of an ultrasonic endoscope according to the present embodiment. FIG. 10 is a partial sectional view taken along line X-X in FIG. 9, illustrating a distal end portion of the insertion portion of the ultrasonic endoscope. FIG. 11 is a schematic partial longitudinal sectional view of the distal end portion of the insertion portion of the ultrasonic endoscope shown in FIGS. 9 and 10.

As illustrated in FIGS. 9 and 10, the ultrasonic endoscope 212 according to the present embodiment is a radial-type ultrasonic endoscope that includes an ultrasonic transducer unit 246 in the ultrasonic observation portion 236 of the distal end portion 240. The ultrasonic transducer unit 246 includes an ultrasonic transducer array 250 in which a plurality of ultrasonic transducers 248 are cylindrically arranged. In the example shown in FIGS. 9 and 10, the ultrasonic observation portion 236 is disposed on the distal end side of the ultrasonic endoscope 212 relative to the endoscopic observation portion 238.

As with the ultrasonic endoscope 12 of the first embodiment shown in FIGS. 1 to 3, the ultrasonic endoscope 212 according to the present invention may include a mechanism for leading out treatment tools, such as forceps, a puncture needle, and a high-frequency knife. A treatment tool lead-out port (not shown), from which these treatment tools are led out, may be formed on the distal end side or on the proximal end side of the ultrasonic endoscope 212 relative to the plurality of ultrasonic transducers 248.

The endoscopic observation portion 238 of the ultrasonic endoscope 212 according to the present embodiment has a structure similar to that of the endoscopic observation portion 38 of the ultrasonic endoscope 12 of the first embodiment shown in FIGS. 2 and 3. As a matter of course, the endoscopic observation portion 238 has an observation window (88), an objective lens (90), a solid-state imaging element (92), an illumination window (94), a cleaning nozzle (96), a wiring cable (98), and the like.

As illustrated in FIGS. 9 and 10, the ultrasonic observation portion 236 according to the present embodiment is composed of the ultrasonic transducer unit 246, an exterior member 241 for attaching and holding the ultrasonic transducer unit 246, and the cable portion 70 including the plurality of coaxial cables 71 that are wired to the ultrasonic transducer unit 246.

In the example shown in FIG. 10, the ultrasonic transducer unit 246 has the ultrasonic transducer array 250 in which the plurality of ultrasonic transducers 248 are cylindrically arranged, an electrode portion 200 that is electrically continuous with the ultrasonic transducer array 250, a backing material layer 252 that supports the ultrasonic transducers 248 of the ultrasonic transducer array 250 from a side of a surface on the central side of the ultrasonic transducer unit 246 (inner surfaces of the ultrasonic transducer 248), an acoustic matching layer 264 that is laminated on a side opposite to the backing material layer 252 with respect to the ultrasonic transducer array 250 (outer side of the ultrasonic transducer array 250), and an acoustic lens 266 that is laminated on a side opposite to the ultrasonic transducer array 250 with respect to the acoustic matching layer 264 (outer side of the acoustic matching layer 264). As described above, the ultrasonic transducer unit 246 has a laminated body 247 that is composed of the acoustic lens 266, the acoustic matching layer 264, the ultrasonic transducer array 250, and the backing material layer 252.

The ultrasonic transducers 248, the ultrasonic transducer array 250, the backing material layer 252, the acoustic matching layer 264, the acoustic lens 266, and the laminated body 247 according to the present embodiment differ in shape but do not differ in structure and function from the ultrasonic transducers 48, the ultrasonic transducer array 50, the backing material layer 52, the acoustic matching layer 64, the acoustic lens 66, and the laminated body 47 of the first embodiment shown in FIGS. 2 and 3. Therefore, description of these elements will be omitted.

The ultrasonic transducer unit 246 has an annular plate 202 that is disposed in such a way that a side surface thereof on the distal end side of the ultrasonic endoscope 212 contacts a side surface of the backing material layer 252 on the distal end side of the ultrasonic endoscope 212 and that fixes the position of a cylindrical member 204 (described below); a support plate 203 that is a disk-shaped plate having an outside diameter larger than the inside diameter of the annular plate 202; the cylindrical member 204 that contacts a surface of the backing material layer 252 on a side opposite to the ultrasonic transducer array 250 (inside of the backing material layer 252), that is joined to the support plate 203 at an end surface thereof on the distal end side of the ultrasonic endoscope 212, and that supports the laminated body 247; a wiring board 254 that is disposed on an outer peripheral portion of the cylindrical member 204 on the proximal end side of the ultrasonic endoscope 212 relative to the backing material layer 252 and that is electrically connected to the plurality of coaxial cables 71 of the cable portion 70 and the electrode portion 200; and a copper foil 262 (first heat conductive member) that is disposed along the side surfaces of the plurality of ultrasonic transducers 248 and the backing material layer 252 on the proximal end side of the ultrasonic endoscope 212 and that is thermally connected to the shield member 73 of the cable portion 70. As in the example shown in FIGS. 10 and 11, the electrode portion 200 and the wiring board 254 are electrically connected to each other by using a wiring cable 208 or the like.

The electrode portion 200 of the ultrasonic transducer unit 246 has individual electrodes 200a for transmitting and receiving voltage signals, such as drive signals and ultrasonic echo signals, to and from the plurality of ultrasonic transducers 248, and a transducer ground 200b that is a ground electrode for the plurality of ultrasonic transducers 248. In the example shown in FIG. 10, each of the individual electrodes 200a is disposed so as to be lead out from an end portion of the ultrasonic transducer 248 on an inner side and on the proximal end side of the ultrasonic transducer 248 to an end surface of the backing material layer 252 on the proximal end side, and the individual electrode 200a is electrically connected to a plurality of electrode pads 205 (described below) of the wiring board 254. Although not illustrated, the transducer ground 200b is electrically connected to a grounded portion in the ultrasonic endoscope 212 by using a lead wire or the like. As described below, because the plurality of electrode pads 205, which are electrically connected to the plurality of individual electrodes 200a of the electrode portion 200, are electrically continuous with the signal wires 71a of the plurality of coaxial cables 71, the plurality of individual electrodes 200a of the electrode portion 200 are electrically continuous with the signal wires 71a of the coaxial cables 71.

Because the transducer ground 200b is a ground electrode for the plurality of ultrasonic transducers 248, preferably, the ground potentials thereof are the same potential. Preferably, the transducer ground 200b is a common electrode for the plurality of ultrasonic transducers 248. Moreover, provided that the transducer ground 200b can be electrically connected to a grounded portion, the transducer ground 200b need not be electrically continuous with the shield layers 71c of the plurality of coaxial cables 71. The positions of the plurality of individual electrodes 200a and the transducer ground 200b are not limited to those shown in FIG. 10, provided that the individual electrodes 200a and the transducer ground 200b can be connected to the signal wires and the ground portion. That is, the positions may be on parts of the ultrasonic transducer 248 on the distal end side of the ultrasonic endoscope 212, or over the entireties of the inner surface and the outer surface of the ultrasonic transducer 248; or the positions may be changed as appropriate in accordance with the structure of the ultrasonic observation portion 236.

As illustrated in FIGS. 10 and 11, the wiring board 254 of the ultrasonic transducer unit 246 is disposed on an outer peripheral portion of the cylindrical member 204 on the proximal end side of the backing material layer 252 and is electrically connected to the electrode portion 200. The wiring board 254 has the plurality of electrode pads 205 that are disposed in a portion thereof on the distal end side of the ultrasonic endoscope 212 (distal end side of the wiring board 254), a wiring portion 256 that is disposed in a portion thereof on the proximal end side of the wiring board 254 relative to the plurality of electrode pads 205, and a ground portion 260 that is disposed in a portion of the wiring board 254 on the most proximal end side. The electrode pads 205 are members each of which is to be connected to a corresponding one of the plurality of individual electrodes 200a of the electrode portion 200. The wiring portion 256 is composed of a plurality of connection portions 258 that are terminals that are electrically continuous with the plurality of electrode pads 205 via wiring (not shown) formed in the wiring board 254 and that are electrically connected to the signal wires 71a of the plurality of coaxial cables 71. The ground portion 260 is electrically connected to the shield layers 71c of the plurality of coaxial cables 71.

The wiring board 254 may be any appropriate member that can electrically connect the plurality of individual electrodes 200a of the electrode portion 200 and the signal wires 71a of the plurality of coaxial cables 71. An FPC may be used as the wiring board 254, or the wiring board 254 may have a cylindrical shape that surrounds the cylindrical member 204. In a case where, for example, the number of the plurality of ultrasonic transducers 248 (the number of channels the ultrasonic transducer array 250) is large, a plurality of the wiring boards 254 may be disposed, and the wiring boards 254 may be arranged side by side so as to surround the cylindrical member 204.

The support plate 203 of the ultrasonic transducer unit 246 is a disk-shaped plate that is disposed in contact with a surface of the annular plate 202 on a side opposite to the backing material layer 252 and that has an outside diameter larger than the inside diameter of the annular plate 202. The support plate 203 fixes the positions of the annular plate 202 and the cylindrical member 204. Therefore, in order to fix the position of the cylindrical member 204, preferably, the support plate 203 is joined to the cylindrical member 204, or may be a member that is integrated with the cylindrical member 204. Moreover, in a case where the support plate 203 is joined to the cylindrical member 204, in order to fix the position of the cylindrical member 204, preferably, the support plate 203 is joined also to the annular plate 202. The shape of the support plate 203 is not limited to a disk-like shape and may be any appropriate shape, such as a polygonal shape, provided that the support plate 203 can fix the positions of the annular plate 202 and the cylindrical member 204.

The cylindrical member 204 of the ultrasonic transducer unit 246 is disposed in contact with the inner surface of the backing material layer 252, the inner surface of the annular plate 202, and a surface of the support plate 203 on a side opposite to the distal end side of the ultrasonic endoscope, and fixes the laminated body 247. Parts of the plurality of coaxial cables 71 of the cable portion 70 on the distal end side are disposed in a space in the cylindrical member 204 on the proximal end side and on the central side of the ultrasonic transducer unit 246 (inside of the cylindrical member 204). Moreover, a plurality of slits 206, for leading out the plurality of coaxial cables 71 toward the outer peripheral side of the cylindrical member 204, are formed in a portion of the cylindrical member 204 on the proximal end side of the backing material layer 252. The cylindrical member 204 may be made of any appropriate material such as a metal or a resin, provided that the cylindrical member 204 can support the laminated body 247.

The copper foil 262 of the ultrasonic transducer unit 246 is a member that is disposed along the side surfaces of the plurality of ultrasonic transducers 248 and the backing material layer 252 on the proximal end side and that conducts heat generated in the plurality of ultrasonic transducers 248. Moreover, in the example shown in FIGS. 10 and 11, a part of the copper foil 262 is extended and is electrically connected to the shield member 73 of the cable portion 70. Therefore, heat generated in the plurality of ultrasonic transducers 248 can be dissipated to the proximal and side of the cable portion 70 via the shield member 73 of the cable portion 70.

As with the copper foil 62 according to the first embodiment shown in FIGS. 3, 4, and 6 to 8, the extended portion of the copper foil 262 may be made of a material different from that of a portion of the copper foil 262 that is disposed along the ultrasonic transducer array 250 and the backing material layer 252. That is, provided that the copper foil 262 and the shield member 73 of the cable portion 70 can be electrically or thermally connected to each other, a portion of the copper foil 262 that contacts the ultrasonic transducer array 250 and the backing material layer 252 may be connected to the shield member 73 of the cable portion 70 by using a lead wire or a mesh-shaped electroconductive member. Moreover, the copper foil 262 may be replaced with a metal member made of a metal having high heat conductivity, such as aluminum, gold, or silver; a heat conductive silicone sheet; or the like. In a case where an electroconductive member is used, the copper foil 262 or a heat conductive member that is used instead of the copper foil 262 can be grounded. In this case, noise received from the outside by the copper foil 262 or a heat conductive member that is used instead of the copper foil 262 can be prevented from entering the plurality of ultrasonic transducers 248.

In the example shown in FIG. 11, as in the example of the first embodiment shown in FIG. 4, the second heat conductive member 80 is disposed between the first insulation tube 74 and the connection pipe 76 of the cable portion 70. Therefore, heat that has been conducted from the copper foil 262 to the shield member 73 of the cable portion 70 can be conducted to the connection pipe 76 and dissipated. In FIG. 11, which is a figure that is simplified for convenience of description as with FIG. 4, only the ultrasonic transducer unit 246 and the cable portion 70 are illustrated, and the other elements are omitted.

The plurality of electrode pads 205 of the wiring board 254 are disposed on the distal end side of the wiring board 254 and are electrically connected to the plurality of individual electrodes 200*a* of the electrode portion 200 by using the wiring cable 208 or the like. The plurality of electrode pads 205 are each electrically continuous with a corresponding one of the plurality of connection portions 258 of the wiring portion 256 via wiring (not shown) formed in the wiring board 254. In the ultrasonic transducer unit 246, even in a case where a plurality of the wiring boards 254 are wired, if a large number of electrode pads 205 are disposed because, for example, the number of channels the ultrasonic transducer array 250 is large, the electrode pads 205 may be arranged in multiple rows. Wiring means for wiring the plurality of electrode pads 205 and the plurality of individual electrodes 200*a* is not limited to the wiring cable 208 illustrated in the figures. Known wiring means, such as lead wires or a FPC, may be used, provided that the wiring means can electrically connect the plurality of electrode pads 205 and the plurality of individual electrodes 200*a*.

The wiring portion 256 of the wiring board 254 is composed of the plurality of connection portions 258, which are terminals each of which is wired to a corresponding one of the signal wires 71*a* of the plurality of coaxial cables 71 of the cable portion 70. In the example shown in FIGS. 10 and 11, the wiring portion 256 is disposed between the plurality of electrode pads 205 and the ground portion 260 of the wiring board 254. Preferably, the total number of the plurality of connection portions 258 of the wiring portion 256 is at least larger than or equal to the total number of the plurality of electrode pads 205. In a case where, for example, the number of channels the ultrasonic transducer array 250 is large, as with the plurality of electrode pads 205, the connection portions 258 may be arranged in multiple rows. Although not illustrated, preferably, wiring portions between the signal wires 71*a* of the plurality of coaxial cables 71 of the cable portion 70 and the plurality of connection portions 258 of the wiring portion 256 are covered by a filler (not shown) made of an insulating resin or the like, in order to prevent wire breakage at the wiring portions.

The ground portion 260 of the wiring board 254 is an electroconductive member that is disposed on the proximal end side of the wiring board 254 and that is electrically connected to the shield layers 71*c* of the plurality of coaxial cables 71 of the cable portion 70. In the example shown in FIGS. 10 and 11, the shield layers 71*c* of the plurality of coaxial cables 71 are electrically connected to the ground portion 260. Accordingly, in order to make the ground potentials of the shield layers 71*c* of the coaxial cables 71 be the same potential, preferably, ground portions 260 to which the shield layers 71*c* of the coaxial cables 71 are electrically connected are electrically continuous with each other. That is, for example, the ground portion 260 may have an annular shape so as to surround the cylindrical member 204. In a case where a plurality of wiring boards 254 are provided, the ground portions 260 of the wiring boards 254 may be electrically connected to each other by using lead wires or the like. In this case, for example, even in a case where the transducer ground 200*b* of the electrode portion 200 is not a common electrode but includes electrodes that are independent from each other, the ground potentials of the plurality of ultrasonic transducers 248 can be made to be the same potential.

In the example of the heat dissipation structure of the present embodiment described above with reference to FIGS. 9 to 11, as in the example of the first embodiment shown in FIG. 4, heat generated in the plurality of ultrasonic transducers 248 can be dissipated to the shield member 73 and the connection pipe 76 of the cable portion 70. Moreover, in the heat dissipation structure of the first embodiment shown in FIGS. 6 to 8, by applying the radial-type ultrasonic transducer unit 246 shown in FIGS. 9 to 11, the ultrasonic endoscope 212 having the radial-type ultrasonic transducer unit 246 can have a heat dissipation structure similar to that described in the first embodiment.

Figure 12:
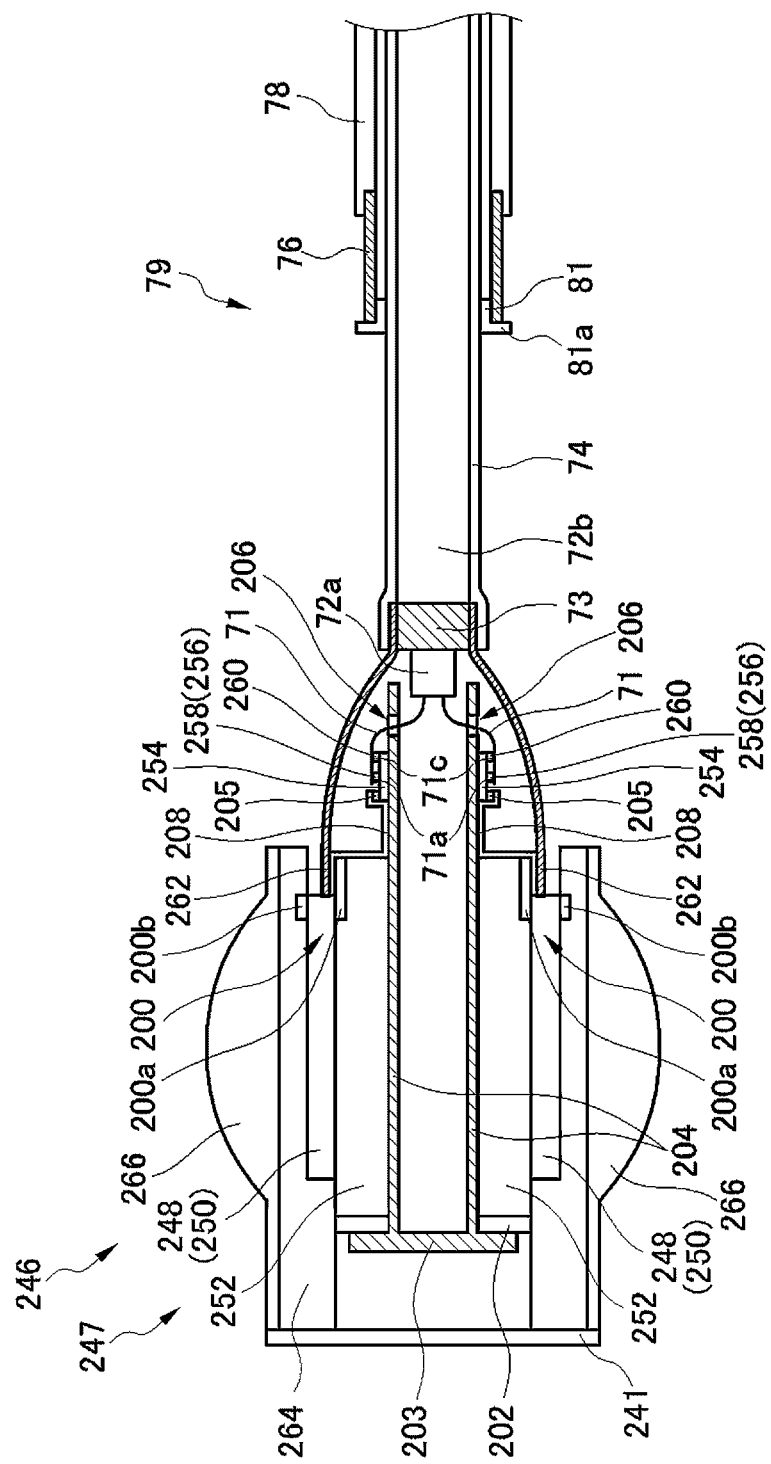
FIG. 12 is a partial longitudinal sectional view of another example of the distal end portion of the insertion portion of the ultrasonic endoscope according to the second embodiment of the present invention.

For example, in another example of the present embodiment shown in FIG. 12, the radial-type ultrasonic transducer unit 246 shown in FIGS. 10 and 11 is connected to the cable portion 79 of the example of the first embodiment shown in FIG. 6. Therefore, in the structure shown in FIG. 12, as in the structure of the example of the first embodiment shown in FIG. 6, because the second heat conductive member 81 of the cable portion 79 has the outward flange 81*a*, the heat dissipation path from the second heat conductive member 81 to the connection pipe 76 is large, and the heat dissipation efficiency is improved. Moreover, because the outward flange 81*a* of the second heat conductive member 81 serves as a retainer of the connection pipe 76, a portion of the cable portion 70 inside of the connection pipe 76 can be prevented from moving toward the distal end side relative to the connection pipe 76.

Figure 13:
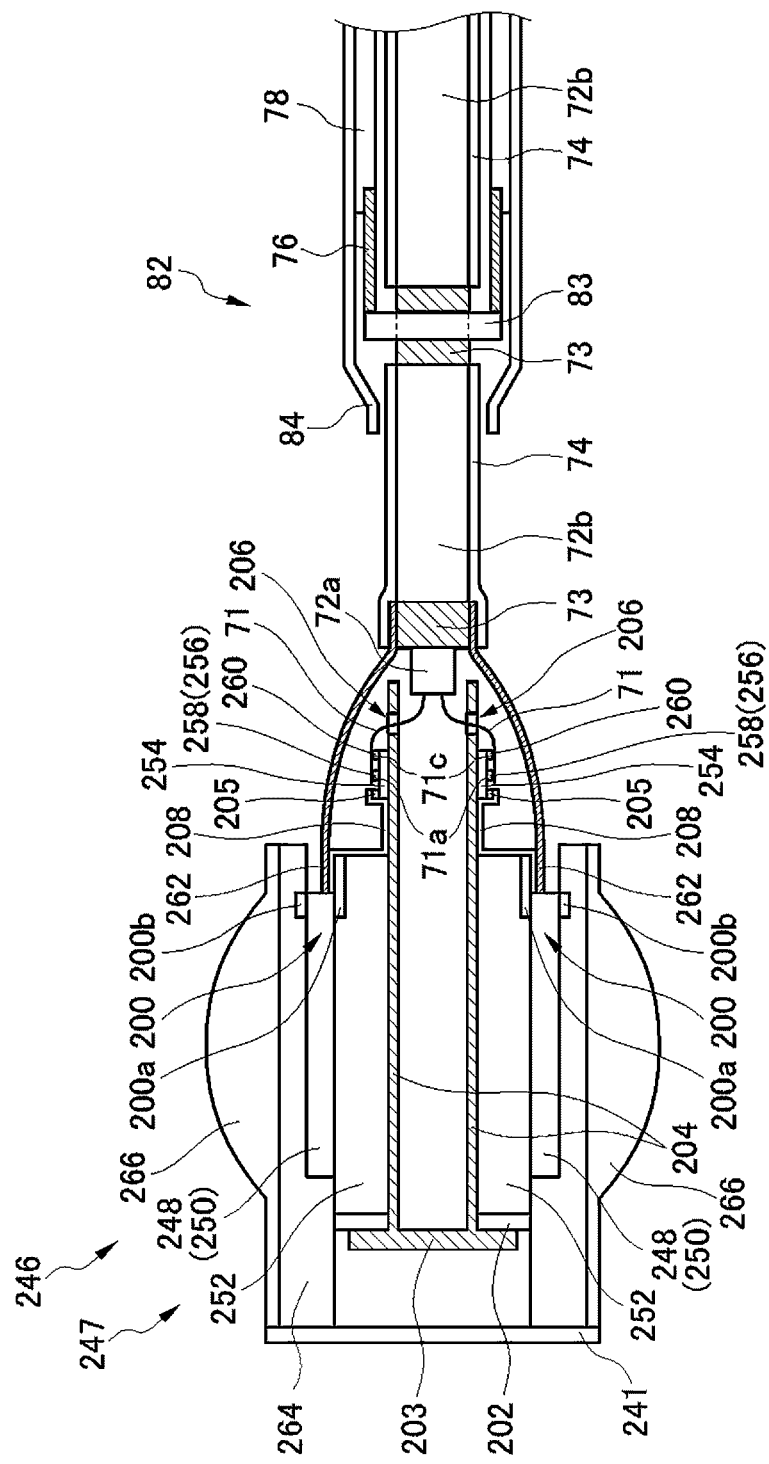
FIG. 13 is a partial longitudinal sectional view of another example of the distal end portion of the insertion portion of the ultrasonic endoscope according to the second embodiment of the present invention.

In another example of the present embodiment shown in FIG. 13, the radial-type ultrasonic transducer unit 246 shown in FIGS. 10 and 11 is connected to the cable portion 82 of the example of the first embodiment shown in FIG. 7. Therefore, with the structure shown in FIG. 13, as in the example of the structure of the first embodiment shown in FIG. 7, the heat dissipation effect can be improved. That is, in a portion of the cable portion 82 where the second heat conductive member 83 is disposed, the first insulation tube 74 and the outer jacket 72b are removed and the second heat conductive member 83 and the shield member 73 of the cable portion 82 contact each other, and therefore it is possible to improve the efficiently in conducting heat, which is conducted from the copper foil 262 to the shield member 73 of the cable portion 82, to the connection pipe 76. Therefore, as with the example of the first embodiment shown in FIG. 7, heat dissipation efficiency can be improved.

Figure 14:
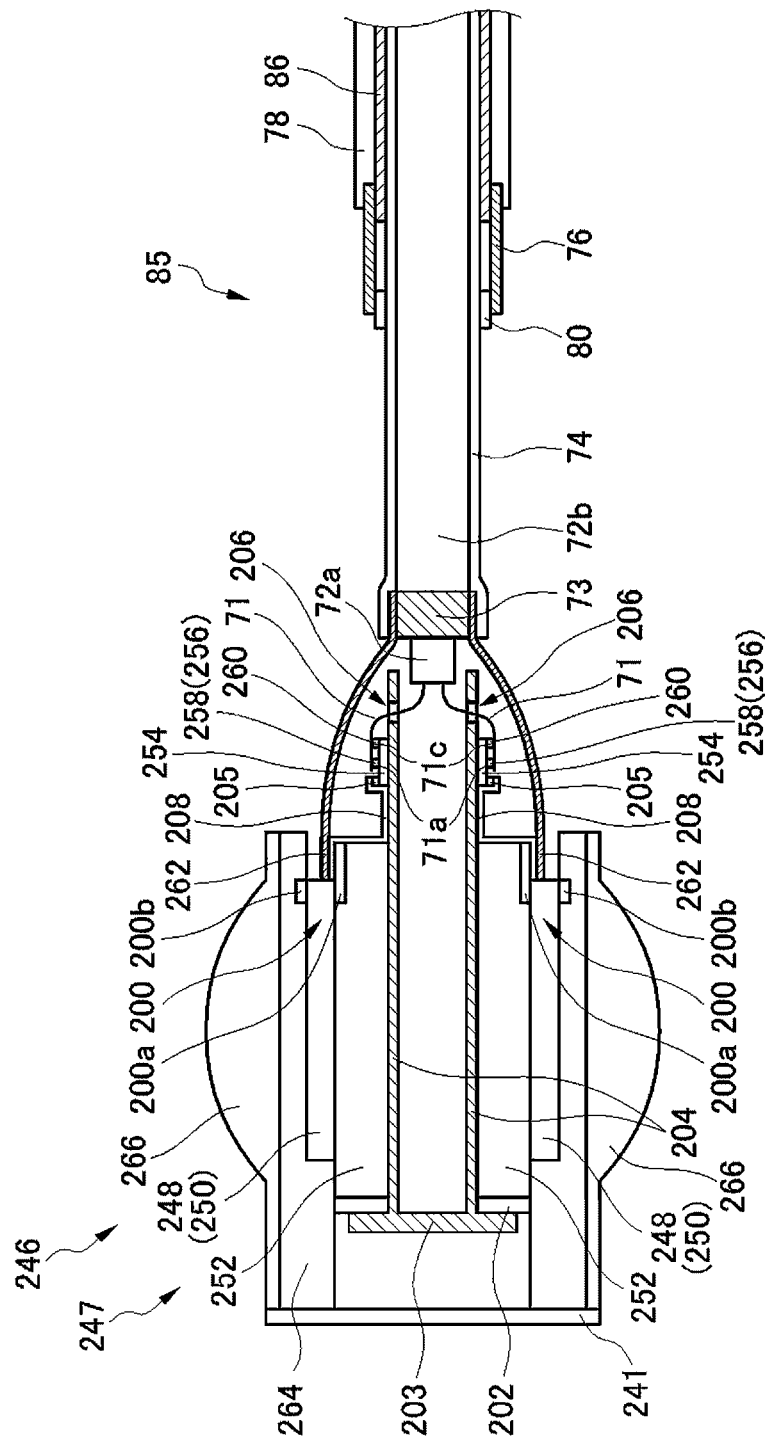
FIG. 14 is a partial longitudinal sectional view of another example of the distal end portion of the insertion portion of the ultrasonic endoscope according to the second embodiment of the present invention.

In another example of the present embodiment shown in FIG. 14, the radial-type ultrasonic transducer unit 246 shown in FIGS. 10 and 11 is connected to the cable portion 85 of the example of the first embodiment shown in FIG. 8. Therefore, with the structure shown in FIG. 14, as with the example of the structure of the first embodiment shown in FIG. 8, the third heat conductive member 86 is disposed so as to fill a space between the first insulation tube 74, and at least a part of the connection pipe 76 and the second insulation tube 78. Therefore, heat that is generated in the plurality of ultrasonic transducers 248 and conducted to the shield member 73 of the cable portion 85 via the copper foil 262 can be dissipated to the connection pipe 76 and the third heat conductive member 86. Accordingly, as with the example of the first embodiment shown in FIG. 8, heat dissipation paths can be increased, and the heat dissipation efficiency can be improved.

Heretofore, ultrasonic endoscopes each having a heat dissipation structure according to the present invention have been described. However, the present invention is not limited to the examples described above, and, as a matter of course, may be improved or modified in various ways within the spirit and scope of the present invention. As a matter of course, the embodiments and the plurality of examples described above may be used in combination as appropriate.

REFERENCE SIGNS LIST 10 ultrasonic inspection system
12, 212 ultrasonic endoscope
14 ultrasonic processor device
16 endoscope processor device
18 light source device
20 monitor
21a water supply tank
21b suction pump
22 insertion portion
24 operating unit
26 universal cord
28a air/water supply button
28b suction button
29 angle knob
30 treatment tool insertion port (forceps port)
32a ultrasound connector
32b endoscope connector
32c light source connector
34a air/water supply tube
34b suction tube
36, 236 ultrasonic observation portion
38, 238 endoscopic observation portion
40, 240 distal end portion
41, 241 exterior member
42 bending portion
43 soft portion
44 treatment tool lead-out port
45 treatment tool channel
46, 246 ultrasonic transducer unit
47, 247 laminated body
48, 248 ultrasonic transducer
50, 250 ultrasonic transducer array
52, 252 backing material layer
54, 254 wiring board
56, 256 wiring portion
58, 258 connection portion
60, 260 ground portion
62, 262 copper foil (first heat conductive member)
64, 264 acoustic matching layer
66, 266 acoustic lens
68 filler layer
70, 79, 82, 85 cable portion
71 coaxial cable
71a signal wire
71b, 71d, 72a, 72b jacket
71c shield layer
73 shield member
74 first insulation tube
76 connection pipe
78 second insulation tube
80, 81, 83 second heat conductive member
81a outward flange
84 insulating layer
86 third heat conductive member
88 observation window
90 objective lens
92 solid-state imaging element
94 illumination window
96 cleaning nozzle
98, 208 wiring cable
200 electrode portion
200a individual electrode
200b transducer ground
202 annular plate
203 support plate
204 cylindrical member
205 electrode pad
206 slit
EL longitudinal direction (elevation direction)
AZ parallel direction (azimuth direction)

What is claimed is:

1. An ultrasonic endoscope comprising:
a laminated body that comprises
an ultrasonic transducer array in which a plurality of ultrasonic transducers are arranged, and
a backing material layer that supports the plurality of ultrasonic transducers;
a cable portion that comprises
a plurality of cables each of which is electrically connected to a corresponding one of the plurality of ultrasonic transducers, and
a shield member that covers the plurality of cables from outside and that is made of a metal;
a first heat conductive member that is disposed on a side surface of the laminated body;
a first insulation tube that covers the shield member of the cable portion;
an electroconductive connection pipe that covers a part of the first insulation tube on a proximal end side of the ultrasonic endoscope;
a second insulation tube that is connected to one end of the connection pipe on the proximal end side and that covers a part of the connection pipe and a part of the first insulation tube on the proximal end side of the ultrasonic endoscope; and a second heat conductive member that is disposed in contact with both of the first insulation tube and the connection pipe, wherein the first heat conductive member is extended to the shield member that is grounded to a housing and is thermally connected to the shield member.

2. The ultrasonic endoscope according to claim 1, wherein the second heat conductive member fills at least a part of a space between the first insulation tube and the connection pipe.

3. The ultrasonic endoscope according to claim 2, wherein the second heat conductive member is a cylindrical member that is disposed between the first insulation tube and the connection pipe.

4. The ultrasonic endoscope according to claim 1, wherein the second heat conductive member has a thick portion at an end portion thereof on a distal end side of the ultrasonic endoscope, the thick portion being thicker than a portion thereof that is disposed between the first insulation tube and the connection pipe, and the thick portion contacts an end surface of the connection pipe on the first heat conductive member side.

5. The ultrasonic endoscope according to claim 2, wherein the second heat conductive member has a thick portion at an end portion thereof on a distal end side of the ultrasonic endoscope, the thick portion being thicker than a portion thereof that is disposed between the first insulation tube and the connection pipe, and the thick portion contacts an end surface of the connection pipe on the first heat conductive member side.

6. The ultrasonic endoscope according to claim 3, wherein the second heat conductive member has a thick portion at an end portion thereof on a distal end side of the ultrasonic endoscope, the thick portion being thicker than a portion thereof that is disposed between the first insulation tube and the connection pipe, and the thick portion contacts an end surface of the connection pipe on the first heat conductive member side.

7. The ultrasonic endoscope according to claim 4,
wherein the second heat conductive member comprises a cylindrical portion and the thick portion, the cylindrical portion being disposed between the first insulation tube and the connection pipe, and
wherein the thick portion is an outward flange that has a cylindrical shape having an outside diameter larger than or equal to an inside diameter of the connection pipe.

8. The ultrasonic endoscope according to claim 5,
wherein the second heat conductive member comprises a cylindrical portion and the thick portion, the cylindrical portion being disposed between the first insulation tube and the connection pipe, and
wherein the thick portion is an outward flange that has a cylindrical shape having an outside diameter larger than or equal to an inside diameter of the connection pipe.

9. The ultrasonic endoscope according to claim 6,
wherein the second heat conductive member comprises a cylindrical portion and the thick portion, the cylindrical portion being disposed between the first insulation tube and the connection pipe, and
wherein the thick portion is an outward flange that has a cylindrical shape having an outside diameter larger than or equal to an inside diameter of the connection pipe.

10. The ultrasonic endoscope according to claim 1,
wherein the cable portion has a jacket of one layer outside of the shield member, and
wherein the jacket of the cable portion is removed at least at a portion that is covered by the second heat conductive member together with the first insulation tube.

11. The ultrasonic endoscope according to claim 2,
wherein the cable portion has a jacket of one layer outside of the shield member, and
wherein the jacket of the cable portion is removed at least at a portion that is covered by the second heat conductive member together with the first insulation tube.

12. The ultrasonic endoscope according to claim 3,
wherein the cable portion has a jacket of one layer outside of the shield member, and
wherein the jacket of the cable portion is removed at least at a portion that is covered by the second heat conductive member together with the first insulation tube.

13. The ultrasonic endoscope according to claim 4,
wherein the cable portion has a jacket of one layer outside of the shield member, and
wherein the jacket of the cable portion is removed at least at a portion that is covered by the second heat conductive member together with the first insulation tube.

14. The ultrasonic endoscope according to claim 7,
wherein the cable portion has a jacket of one layer outside of the shield member, and
wherein the jacket of the cable portion is removed at least at a portion that is covered by the second heat conductive member together with the first insulation tube.

15. The ultrasonic endoscope according to claim 10,
wherein the jacket of the cable portion is removed on the distal end side of the connection pipe and the shield member is exposed,
wherein, at a portion where the jacket is removed and the shield member is exposed to the first insulation tube, a part of the first insulation tube is removed, and the shield member is exposed to the outside, and
wherein the second heat conductive member contacts the portion where the shield member is exposed to the outside, covers the removed part of the first insulation tube, and contacts the distal end side of the connection pipe.

16. The ultrasonic endoscope according to claim 11,
wherein the jacket of the cable portion is removed on the distal end side of the connection pipe and the shield member is exposed,
wherein, at a portion where the jacket is removed and the shield member is exposed to the first insulation tube, a part of the first insulation tube is removed, and the shield member is exposed to the outside, and
wherein the second heat conductive member contacts the portion where the shield member is exposed to the outside, covers the removed part of the first insulation tube, and contacts the distal end side of the connection pipe.

17. The ultrasonic endoscope according to claim 12,
wherein the jacket of the cable portion is removed on the distal end side of the connection pipe and the shield member is exposed,
wherein, at a portion where the jacket is removed and the shield member is exposed to the first insulation tube, a part of the first insulation tube is removed, and the shield member is exposed to the outside, and
wherein the second heat conductive member contacts the portion where the shield member is exposed to the outside, covers the removed part of the first insulation tube, and contacts the distal end side of the connection pipe.

18. The ultrasonic endoscope according to claim 15, further comprising:
an insulation layer that is disposed outside of the connection pipe.

19. The ultrasonic endoscope according to claim 1, further comprising:
a third heat conductive member that fills a space between the first insulation tube, and a portion of the connection pipe on the proximal end side and the second insulation tube.

* * * * *